US012678575B2

(12) United States Patent
Luo

(10) Patent No.: US 12,678,575 B2
(45) Date of Patent: Jul. 14, 2026

(54) VENTILATION COMPONENT FOR USE IN AN ANTI-SNORING DEVICE

(71) Applicant: WALLENBERG UNION LLC, Newark, DE (US)

(72) Inventor: David Luo, Newark, DE (US)

(73) Assignee: WALLENBERG UNION LLC, Newark, DE (US)

( * ) Notice: Subject to any disclaimer, the term of this patent is extended or adjusted under 35 U.S.C. 154(b) by 0 days.

(21) Appl. No.: 18/783,681

(22) Filed: Jul. 25, 2024

(65) Prior Publication Data
US 2026/0027310 A1     Jan. 29, 2026

(51) Int. Cl.
*A61M 16/00*        (2006.01)

(52) U.S. Cl.
CPC ..... *A61M 16/0066* (2013.01); *A61M 2205/42* (2013.01)

(58) Field of Classification Search
CPC .......... A61M 16/0066; A61M 16/0012; A61M 2206/11; A61M 2206/20; A61M 2205/42; F04D 29/663–667; F16L 55/02709; F16L 55/02718; F24F 13/24; F24F 2013/242
See application file for complete search history.

(56) References Cited

U.S. PATENT DOCUMENTS

| | | | |
|---|---|---|---|
| 2002/0137981 A1* | 9/2002 | Williams | A61M 60/295 600/18 |
| 2008/0257346 A1* | 10/2008 | Lathrop | A61M 16/0066 181/224 |
| 2009/0050156 A1* | 2/2009 | Ng | A61M 16/0816 128/205.24 |
| 2015/0023782 A1* | 1/2015 | Velzy | A61M 16/0069 415/119 |
| 2017/0259019 A1* | 9/2017 | Cariola | A61M 16/1055 |
| 2021/0001069 A1* | 1/2021 | Higashiyama | A61M 16/0066 |

* cited by examiner

*Primary Examiner* — Joseph D. Boecker
*Assistant Examiner* — Brian T Khong
(74) *Attorney, Agent, or Firm* — Birch, Stewart, Kolasch & Birch, LLP

(57)        ABSTRACT

A ventilation component for use in an anti-snoring device. The ventilation component is provided within a noise-reducing air passage of a machine for the treatment of respiratory-related disorders such as a PAP machine. The internal structure of the ventilation component is formed by baffles arranged at certain intervals. When the ventilation component operates, the gas that enters its interior flows through the gaps between the baffles, where the gas is divided and streamlined to achieve noise reduction. The ventilation component can adopt various structural forms and combinations to reduce noise. It also has the flexibility to alter its shape and structure based on the form of the noise-reducing air passage.

25 Claims, 26 Drawing Sheets

25

24

2

2                                    An Anti-snoring Device

VENTILATION COMPONENT FOR USE IN AN ANTI-SNORING DEVICE

TECHNICAL FIELD

This disclosure pertains to a ventilation component for use in an anti-snoring device, specifically provided within the noise-reducing air passage of a respiratory machine, configured to reduce noise for the air entering the noise-reducing air passage.

BACKGROUND

Sleep apnea is a severe sleep disorder that is typically categorized into three types: obstructive, central, and mixed, with obstructive sleep apnea being the most common. Obstructive sleep apnea/hypopnea occurs when the patient's airway is fully or partially blocked by relaxed muscles and other tissues during sleep. This blockage can be caused by various factors including, but not limited to, relaxation of soft tissues, relaxation of pharyngeal muscles, abnormalities in the uvula and base of the tongue, nasal obstruction, obesity, genetic factors, alcohol and medication use, and poor lifestyle choices. Therefore, the occurrence of obstructive sleep apnea results from the interaction of multiple factors, and understanding and addressing these underlying causes is crucial for effectively managing the condition.

In the treatment of obstructive sleep apnea, PAP (Positive Airway Pressure) therapy is one of the widely adopted methods. Continuous Positive Airway Pressure (CPAP), a common and effective form of PAP therapy, also known as a single-level sleep ventilator, works by delivering a constant airway pressure through a device configured to supply a steady flow of air to the patient's airway via a hose connected to the patient's nose and/or mouth. This positive air flow prevents the airway from collapsing or being obstructed during sleep, maintaining clear breathing and thereby reducing or eliminating occurrences of apneas and breathing obstructions. Beyond CPAP, other treatment methods for obstructive sleep apnea include lifestyle and behavioral changes such as weight loss, avoiding alcohol and sedatives, and improving sleep positions. Additionally, positional therapy is an effective treatment method, which involves changing sleep positions to reduce occurrences of apneas. Oral appliances like mouth guards or mandibular advancement devices can help keep the airway open and reduce obstructions. In some cases, surgery may be necessary, for example, when structural issues in the nasal or oral cavities cause obstructions. However, based on observations and clinical experience, CPAP therapy is considered the most popular and effective non-surgical treatment option. This is because CPAP therapy is a non-invasive, safe, effective, and adjustable method that can significantly improve the patient's sleep quality and quality of life in a short period.

SUMMARY

The objective of this disclosure is to provide a novel ventilation component for use in an anti-snoring device, which achieves noise reduction to FDA regulatory standards while offering a more stable and reliable structure that is also conducive to manufacturing and rapid market adaptation. This ventilation component provided by this disclosure can be used by patients over extended periods and long phases, overcoming the limitations of similar existing technologies. It offers a solution that is more effective, applicable in a broader range of scenarios and spaces, and delivers a simpler, more efficient, and reliable method for providing patients with continuous positive air pressure to treat sleep-related breathing disorders.

In one embodiment, a ventilation component for use in an anti-snoring device is provided. The ventilation component includes an intake end, an exhaust end, baffles, and a peripheral wall. At least one ventilation component is provided within a noise-reducing air passage of a machine for the treatment of respiratory-related disorders and is configured to divide and streamline gas that flows into the noise-reducing air passage. The at least one ventilation component includes an intake end, configured to receive airflow into the at least one ventilation component, and an exhaust end, configured to allow the airflow to exit from the at least one ventilation component. The at least one ventilation component also includes at least one form of baffles spaced at certain intervals, configured to divide the airflow into multiple smaller flow units. In at least one form, the interval between at least two baffles is equal, and the intervals between each baffle create gap channels through which the airflow passes. A peripheral wall surrounds the baffles, and a total area of the gap channels at the exhaust end is at least 0.2 times an area enclosed by the peripheral wall of the at least one ventilation component at the exhaust end. The length-to-width ratio of the at least one ventilation component is between 0.1 to 1.

In one embodiment, the baffles form an angle with a horizontal plane.

In one embodiment, a casing of the noise-reducing air passage includes an inner wall, and a distance between the exhaust end of the at least one ventilation component and its opposing inner wall of the casing is at least 1.5 times the width of the at least one ventilation component.

In one embodiment, two chambers are provided within the noise-reducing air passage, and one or more of the at least one ventilation component communicates with the two chambers, and parts of the one or more of the at least one ventilation component are present within the two chambers.

In one embodiment, the at least one ventilation component includes a rigid material.

In one embodiment, the rigid material includes one or more of the following materials: polypropylene, polycarbonate, polyethylene terephthalate-1,4-cyclohexane dimethanol ester, polyamide, or polyetheretherketone.

In another embodiment, a ventilation component for use in an anti-snoring device is provided. The ventilation component includes an intake end, an exhaust end, baffles, and a peripheral wall. At least one ventilation component is provided within a noise-reducing air passage of a machine for the treatment of respiratory-related disorders and is configured to divide and streamline gas that flows into the noise-reducing air passage. The at least one ventilation component includes an intake end, configured to receive airflow into the at least one ventilation component, and an exhaust end, configured to allow the airflow to exit from the at least one ventilation component. The at least one ventilation component also includes at least one form of baffles spaced at certain intervals, configured to divide the airflow into multiple smaller flow units, and the intervals between each baffle create gap channels through which the airflow passes. A peripheral wall surrounds the baffles, and a total area of the gap channels at the exhaust end is at least 0.2 times an area enclosed by the peripheral wall of the at least one ventilation component at the exhaust end. Straight lines that connect each intake end center to its corresponding exhaust end center of the gap channels are parallel, and a length of the straight lines is at least 10 mm.

In one embodiment, the at least one ventilation component is provided within the noise-reducing air passage such that the gas passes through one or more of the at least one ventilation component in a vertical direction.

In one embodiment, a blower is provided within the noise-reducing air passage, and the direction of the gas that flows through one or more of the at least one ventilation component is parallel to the direction of the gas that enters the blower.

In one embodiment, the blower includes an inlet, and a straight-line distance between the exhaust end of the at least one ventilation component and the blower inlet is less than or equal to 15 mm.

In one embodiment, at least two chambers are provided within the noise-reducing air passage, and one or more of the at least one ventilation component is present only within one of the at least two chambers.

In one embodiment, one or more of the at least one ventilation component and the casing of the noise-reducing air passage are integrally formed.

In yet another embodiment, a ventilation component for use in an anti-snoring device is provided. The ventilation component includes an intake end, an exhaust end, baffles, and a peripheral wall. At least one ventilation component is provided within a noise-reducing air passage of a machine for the treatment of respiratory-related disorders and is configured to divide and streamline gas that flows into the noise-reducing air passage. The at least one ventilation component includes an intake end, configured to receive airflow into the at least one ventilation component, and an exhaust end, configured to allow the airflow to exit from the at least one ventilation component. The at least one ventilation component also includes at least one form of baffles spaced at certain intervals, configured to divide the airflow into multiple smaller flow units, and the intervals between each baffle create gap channels through which the airflow passes. A peripheral wall surrounds the baffles, and a total area of the gap channels at the exhaust end is at least 0.2 times an area enclosed by the peripheral wall of the at least one ventilation component at the exhaust end. A distance from the intake end to the exhaust end of the at least one ventilation component is at least 10 mm. In an orthographic view from a plane of the intake end, baffles of at least two directions are provided, and lines on which baffles of the at least two directions lie intersect each other.

In one embodiment, the distance between the exhaust end of the at least one ventilation component and its opposing inner wall of the casing of the noise-reducing air passage is at least 1.5 times the width of the at least one ventilation component.

In one embodiment, the at least one ventilation component includes a rigid material.

In one embodiment, the at least one ventilation component is provided within the noise-reducing air passage such that the gas passes through one or more of the at least one ventilation component in a horizontal direction.

In one embodiment, a length-to-width ratio of the at least one ventilation component is between 0.1 to 1.

In one embodiment, the baffles of the at least one ventilation component are tapered.

In another embodiment, a ventilation component for use in an anti-snoring device is provided. The ventilation component includes an intake end, an exhaust end, baffles, and a peripheral wall. At least one ventilation component is provided within a noise-reducing air passage of a machine for the treatment of respiratory-related disorders and is configured to divide and streamline gas that flows into the noise-reducing air passage. The at least one ventilation component includes an intake end, configured to receive airflow into the at least one ventilation component, and an exhaust end, configured to allow the airflow to exit from the at least one ventilation component. The at least one ventilation component also includes at least one form of baffles spaced at certain intervals, configured to divide the airflow into multiple smaller flow units, where the intervals between each baffle create gap channels through which the airflow passes. A peripheral wall surrounds the baffles, configured to define an outer shape of the at least one ventilation component to match an inner wall of a casing of the noise-reducing air passage. And at least one gap channel has a draft angle with a range between $0.1°$ to $2°$, and the intervals between the baffles are at least 0.8 mm.

In one embodiment, a blower is provided within the noise-reducing air passage and includes an inlet, and a straight-line distance between the exhaust end of the at least one ventilation component and the blower inlet is less than or equal to 15 mm.

In one embodiment, two chambers are provided within the noise-reducing air passage. One or more of the at least one ventilation component communicates with the two chambers, and parts of the one or more of the at least one ventilation component are present within the two chambers.

In one embodiment, the direction of the gas that flows through one or more of the at least one ventilation component is parallel to the direction of the gas that enters the blower.

In one embodiment, the at least one ventilation component is provided within the noise-reducing air passage, and a distance between the exhaust end of the at least one ventilation component and its opposing inner wall of the casing of the noise-reducing air passage is at least 1.5 times a width of the at least one ventilation component.

In one embodiment, baffles of at least two directions are provided on the at least one ventilation component.

In one embodiment, an opening at the intake end of the at least one ventilation component is larger than an opening at the exhaust end.

The implementation of the ventilation component provided by this disclosure at least includes the following beneficial effects:

1. The ventilation component features a simple and reliable structure that enhances the stability of the noise-reducing air passage, while also being easy to install and reducing costs. Unlike existing market solutions that use foam provided within the noise-reducing air passage for primary noise reduction or complex noise-reducing components made from multiple materials, this disclosure utilizes a ventilation component made from a single material. This simple structure offers clear advantages in terms of structure, cost, production efficiency, and stability. Firstly, the ventilation component of this disclosure can reduce noise by at least 2 decibels, not only providing excellent noise reduction but also achieving regulatory noise level. Its structure, consisting only of a peripheral wall and the baffles surrounded by the peripheral wall, simplifies the form and avoids complex, intricate connections, thus reducing the risk of potential faults and damage due to structural complexity, providing a solid foundation for the long-term stable operation of respiratory machines. Moreover, because of its simple structure, the ventilation component is easier to maintain and repair, reducing the maintenance costs and time for the respiratory-related devices. Secondly, the ventilation component is relatively small in size, making it more convenient to install inside the noise-reducing air passage without occupying excessive space. Multiple ventilation components can also be combined within the air passage, resulting in a more compact overall structure of the respiratory machine. Additionally, the simplicity and ease of installation of the ventilation component allow assembly personnel to easily assemble it, saving time and labor costs during the production phase and further enhancing production efficiency. Furthermore, as the ventilation component is formed from a single material and has a basic structure, it itself is a basic unit component, the manufacturing process is simplified and costs are more controllable. Specifically, due to its simple structure and uniform material, manufacturers can more easily engage in mass production, and due to its separability, producers and developers can further reduce costs through material optimization and process improvements. Consequently, the ventilation component of this disclosure also offers the advantage of lower costs, providing patients with a high cost-effective product while also facilitating technological innovation and cost reduction in the respiratory machine industry.

2. By using accurate scientific data and correct theoretical foundations, the structure of the ventilation component is configured to achieve more efficient noise reduction. (1) After determining the optimal form of the ventilation component, its structure and position data are standardized, and multiple simulations and experiments are conducted to ensure the component achieves optimal performance in this form. First, the area of the gap channels within the ventilation component is specified, as these channels are the sole pathways for air to pass through the chamber within the chamber at its position. Therefore, the size of the gap channels determines whether there is sufficient air flow entering the blower for pressurization, and overly narrow gap channels can produce noise when air flows through them at certain speeds. Thus, the interval between the baffles is set to be greater than 0.8 mm. Conversely, if the gap channels are too large, the baffles cannot function well to reduce noise. Thus, the interval between the baffles is set to be less than 2.2 mm. (2) Additionally, the noise level is also related to the length of the ventilation component (the length of the gap channels). When the gas flows through the ventilation component, although the airflow is divided into smaller flow units by the baffles, gap channels with a too-short length can cause the airflow to immediately recombine after division, making the baffles unable to achieve the intended effect of reducing turbulence and noise, thereby impacting noise reduction. Hence, the length of each gap channel in the ventilation component is set to be at least 10 mm. These data are derived from comparing information and conducting multiple repetitive experiments by placing different forms of ventilation components in the same noise-reducing air passage and then testing different forms of ventilation components used in the first experiment in another noise-reducing air passage. This process yields conclusions that withstand repeated testing, leading to the design of the optimal structure for the ventilation component in this disclosure.

3. The ventilation component exhibits strong adaptability, allowing for flexible application according to different internal structures of noise-reducing air passages, while impacting airflow less and maintaining its fluidity. The core element of the ventilation component lies in its structure configured to divide and streamline airflow for noise reduction, enabling the external shape of the ventilation component to vary as needed. (1) In typical scenarios, to facilitate placement in chambers within the noise-reducing air passage, the ventilation component adopts a rectangular casing. In some cases, when it needs to be positioned within tubes of the air passage such as the inlet pipe, its appearance can be altered to have a circular peripheral wall to fit the pipe. It is evident that the ventilation component can also take on any shape other than rectangular or circular, such as elliptical or conical, based on the internal structure of the noise-reducing air passage. (2) The ventilation components can be freely combined, such that in the orthographic view from the plane of the intake end, the baffles of at least two directions are provided and the lines on which baffles of different directions lie intersect each other, forming a more effective ventilation component combination. There are two possible arrangements for this free combination: either the baffles of different directions are aligned in the line connecting the intake end and exhaust end (with one ventilation component in front of the other), or the baffles of different directions are aligned perpendicular to the line connecting the intake end and exhaust end (with one ventilation component above the other), making the ventilation component more effective and flexible. (3) Additionally, pairing the ventilation component with noise-reducing materials such as foam or silicone can further lower the overall noise of the anti-snoring device. The ventilation component divides larger airflows into smoother streams to reduce noise, while the noise-reducing materials absorb sound energy and convert it into kinetic energy, dissipating noise and achieving further noise reduction. This flexibility allows the ventilation component to adjust according to the internal structure and spatial constraints of the air passage, resulting in better matching and noise reduction effects. Thus, the ventilation component is versatile in form, capable of adapting to various shapes and structures of noise-reducing air passages, providing greater applicability and flexibility for noise reduction treatments. Moreover, delivering breathable gas at a specific pressure and flow rate is a crucial outcome for respiratory devices; therefore, ensuring that the placement of the ventilation component within the noise-reducing air passage does not affect the airflow's pressure and flow is vital for the normal operation of respiratory devices. This disclosure achieves this by calculating the appropriate gap width inside the ventilation component, ensuring that while it reduces noise, it does not hinder the ventilation fluidity, thus ensuring the stability and effectiveness of the respiratory device treatment.

DETAILED DESCRIPTION

Figure 1:
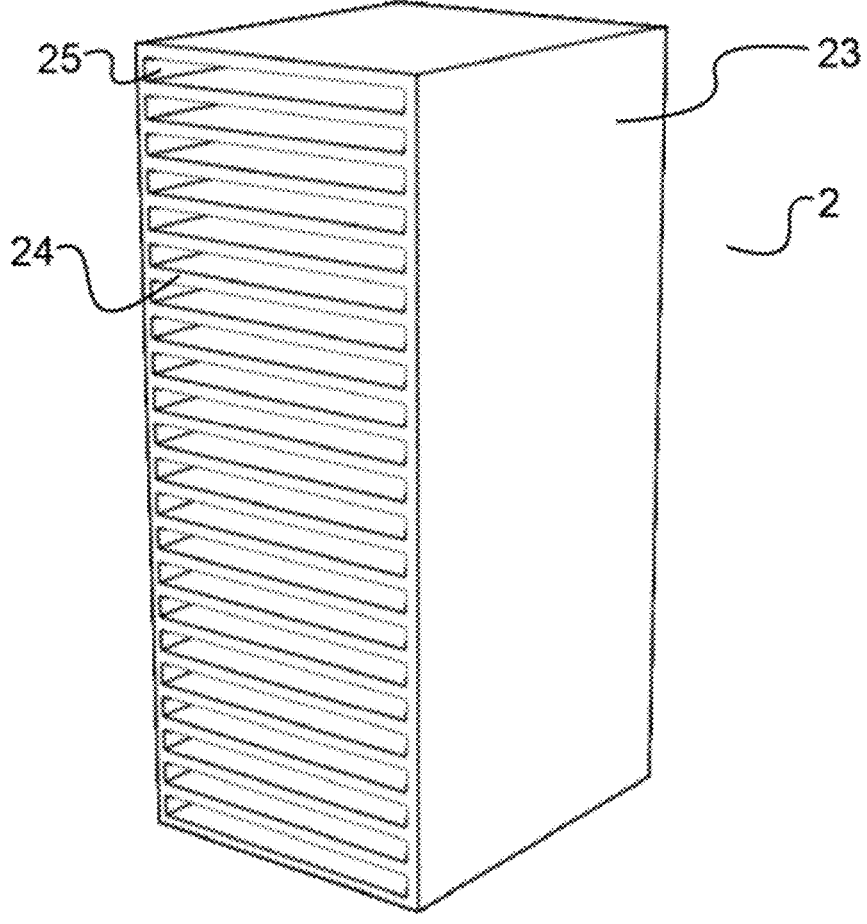
FIG. 1 is a three-dimensional schematic diagram of a ventilation component in accordance with one embodiment.
Figure 2:
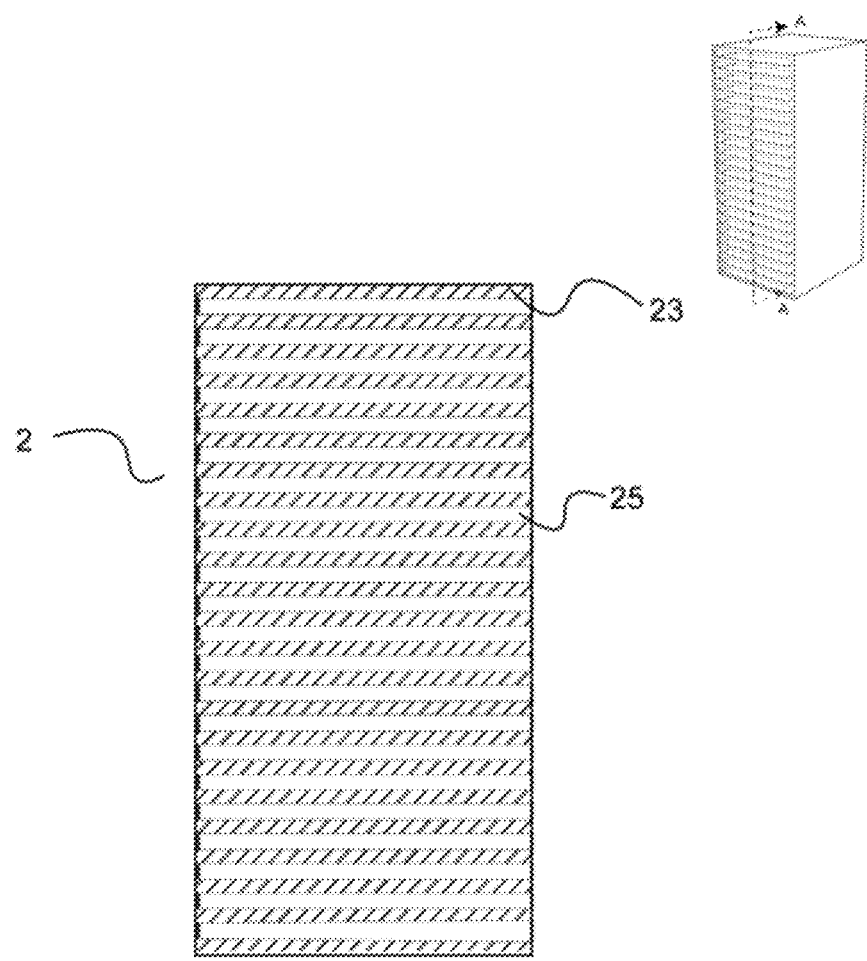
FIG. 2 is a cross-sectional view along line A-A of a ventilation component in accordance with one embodiment.
Figure 3:
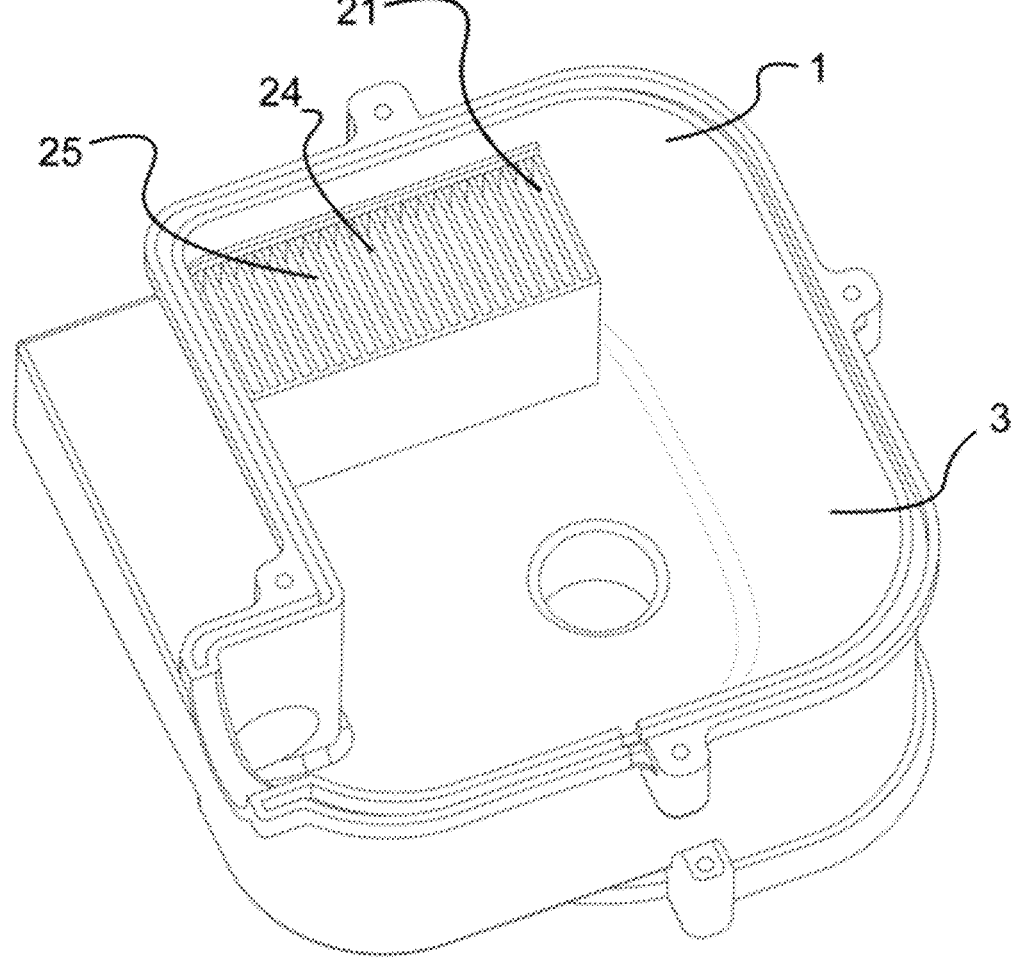
FIG. 3 is a schematic diagram of a ventilation component placed horizontally for use within the noise-reducing air passage in accordance with one embodiment.
Figure 4:
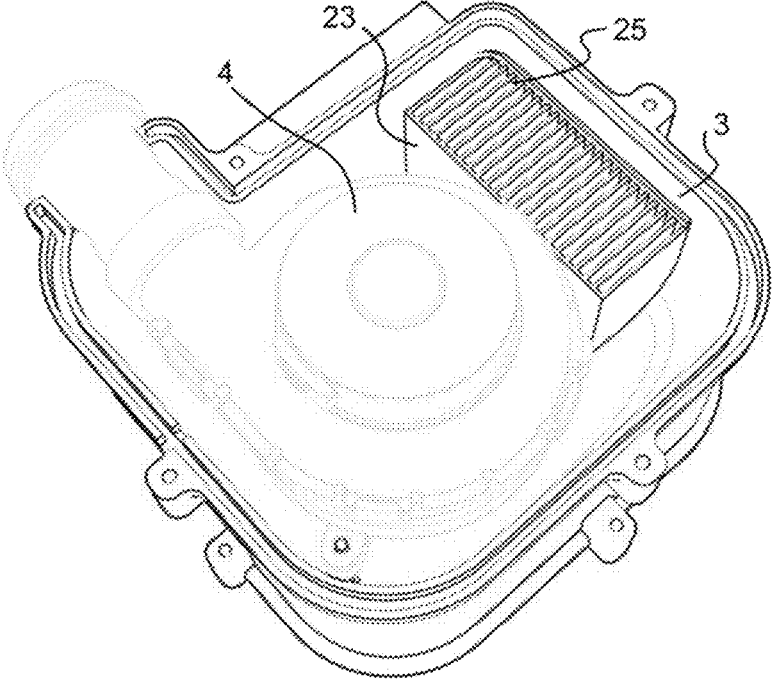
FIG. 4 is a schematic diagram of the use of a ventilation component within a noise-reducing air passage in accordance with one embodiment.

To facilitate the understanding of the disclosure, a more comprehensive description will be provided with reference to the relevant drawings. The drawings illustrate typical embodiments of the disclosure. However, the disclosure can be implemented in many different forms and is not limited to the embodiments described herein. On the contrary, the embodiments are provided to make the disclosure more thorough and comprehensive.

Unless otherwise defined, all technical and scientific terms used herein have the same meaning as commonly understood by one of ordinary skill in the art to which this disclosure belongs. The terms used in the specification of the disclosure herein are for the purpose of describing particular embodiments only rather than limiting the disclosure.

One of the most critical components in CPAP devices is the internal noise-reducing air passage. The noise-reducing air passage system includes a blower and a series of internal structures that work together to provide a constant positive pressure airflow. The blower is the core component of the CPAP device and it generates positive pressure breathable gas and delivers it to the patient's airway. The blower in CPAP devices is typically configured to be compact and efficient, capable of stably producing the required airflow pressure. The internal structures in the noise-reducing air passage play a crucial role, tasked with conveying airflow and reducing noise and vibrations. These components ensure the stability and safety of the airflow. The design and construction of the entire noise-reducing air passage system are critical, as their effectiveness and reliability directly impact the therapeutic outcomes and patient comfort. Therefore, the noise-reducing air passage system of CPAP devices has been carefully designed and rigorously tested to ensure stable, safe, and reliable performance. This efficient noise-reducing air passage system is one of the reasons why CPAP therapy is a preferred treatment method for obstructive sleep apnea.

The present disclosure addresses the issues associated with the complexity of noise-reducing structures within existing market air passages, where noise reduction is typically achieved using foam and the noise-reducing structure has suboptimal noise reduction outcomes. To address these issues, this disclosure provides a more effective, reliable, and structurally simpler ventilation component. The ventilation component provided by this disclosure not only optimizes various disadvantages of existing designs but also achieves regulatory noise levels. Therefore, this disclosure benefits patients, manufacturers, and the market by providing an advanced technical solution. This disclosure also allows for changing the shape of the peripheral wall of the ventilation component to fit more internal structures of the noise-reducing air passages, and the ventilation component can be used in various forms to achieve more advantageous noise reduction effects.

Detailed embodiments are presented below to elucidate the configurations of the ventilation component for use in an anti-snoring device.

Embodiment 1

This embodiment provides a ventilation component 2 for use within a noise-reducing air passage 1 of a respiratory-related device. This embodiment provides three-dimensional views, cross-sectional views, installation diagrams, and schematic diagrams of use of the ventilation component 2, as shown in FIGS. 1-18. This embodiment pertains to a ventilation component 2 for use in anti-snoring devices, at least one of which is provided within a noise-reducing air passage 1 of a machine for treatment of respiratory-related disorders such as a PAP machine, and is configured to divide and streamline gas that flows into the noise-reducing air passage 1. It includes multiple baffles 24 arranged at certain intervals to divide and streamline the airflow, as well as several gap channels 25 to facilitate passage of the airflow through the ventilation component 2. The gap channels 25 are formed by the walls of adjacent baffles 24 and the peripheral wall 23 of the ventilation component 2. The intake end 21 is configured to receive airflow into the ventilation component 2, and the exhaust end 22 is configured to allow airflow to exit from the ventilation component 2, with the distance from the intake end 21 to the exhaust end 22 being at least 10 mm. The ventilation component 2 is made of rigid materials, including polypropylene, polycarbonate, polyethylene terephthalate-1,4-cyclohexane dimethanol ester, polyamide, polyetheretherketone or metals, etc. Both the intake end 21 and the exhaust end 22 have the form of at least one plane, which can be inclined at any angle or be a vertical plane. A blower 4 is provided within the casing of the noise-reducing air passage 1 and the blower 4 includes an inlet.

Figure 5:
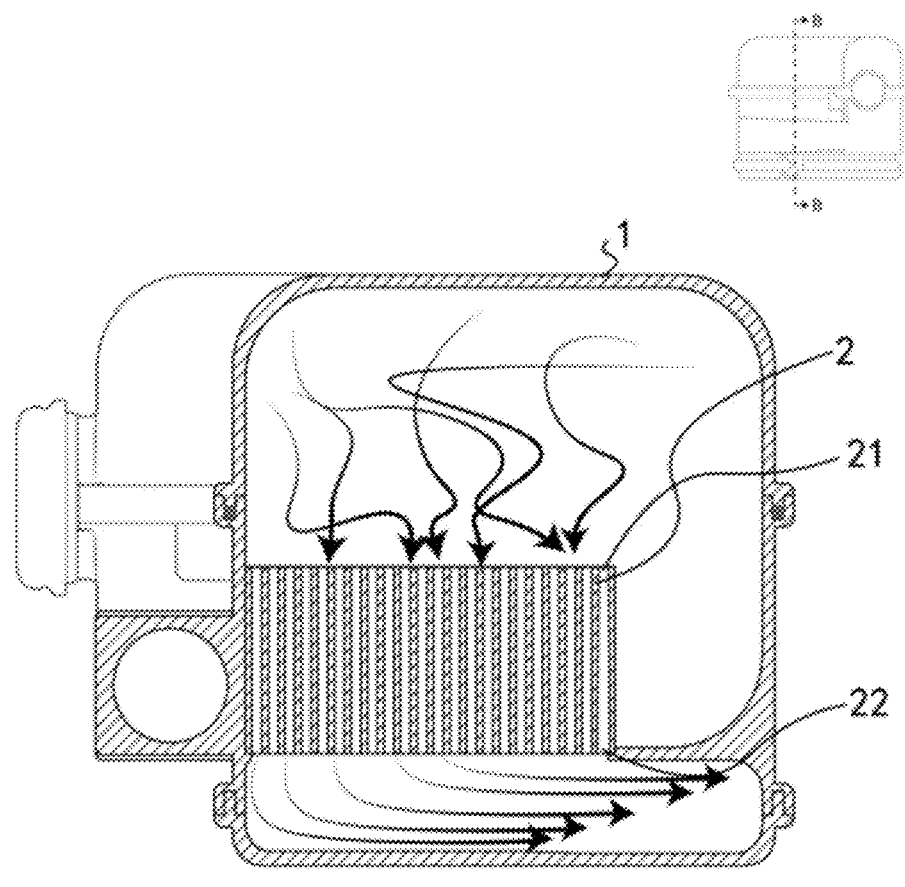
FIG. 5 is a schematic diagram illustrating how a ventilation component streamlines airflow within a noise-reducing air passage in accordance with one embodiment.
Figure 6:
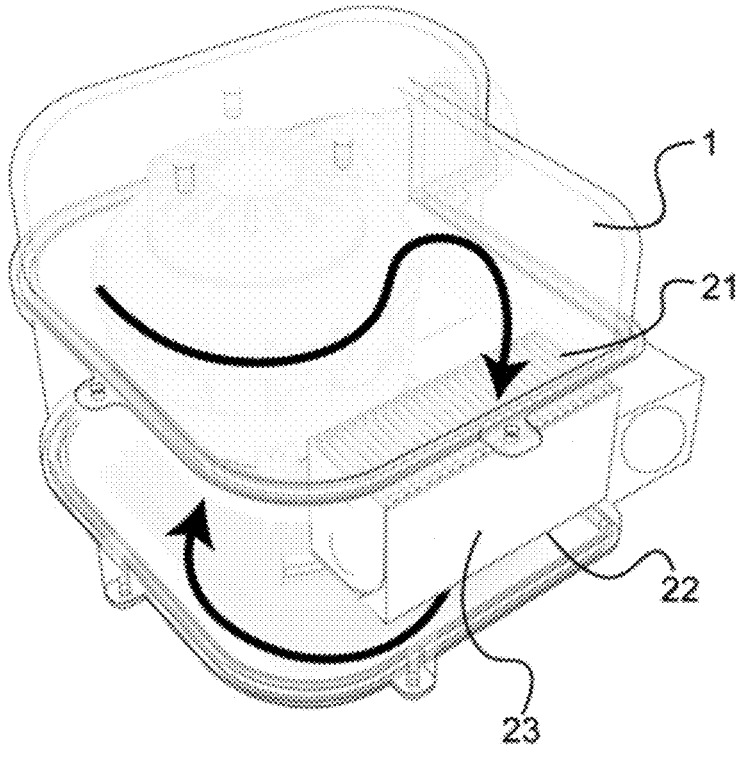
FIG. 6 is a schematic diagram of the airflow direction within a ventilation component in accordance with one embodiment.
Figure 7:
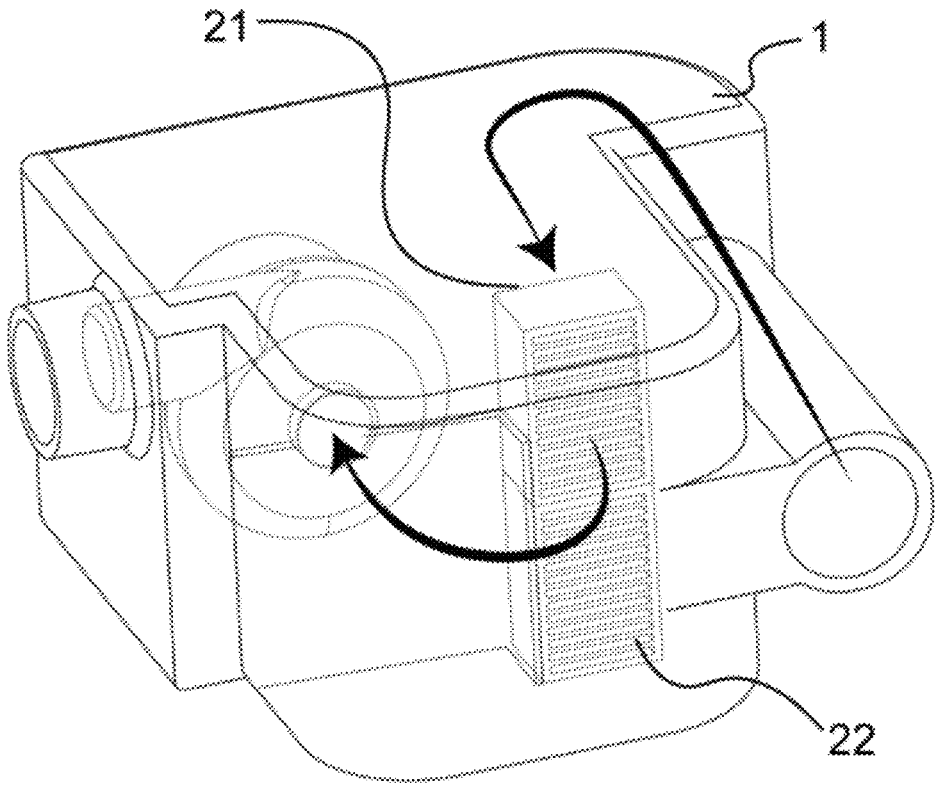
FIG. 7 is a schematic diagram of a ventilation component placed vertically for use within the noise-reducing air passage in accordance with one embodiment.
Figure 8:
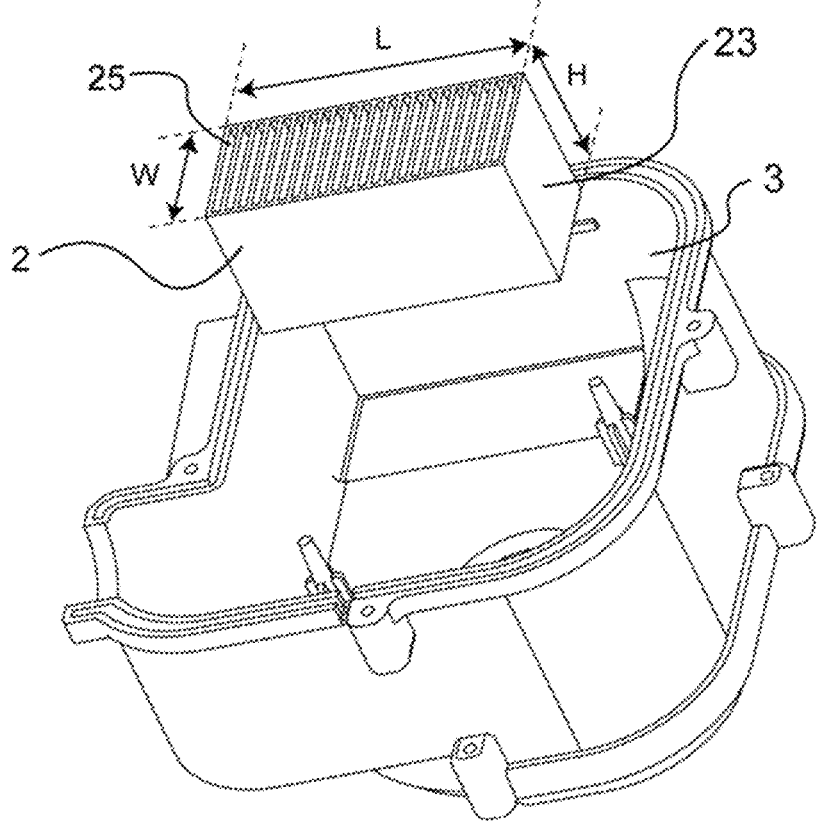
FIG. 8 is a schematic diagram indicating the length, width, and height of a ventilation component in accordance with one embodiment.
Figure 9:
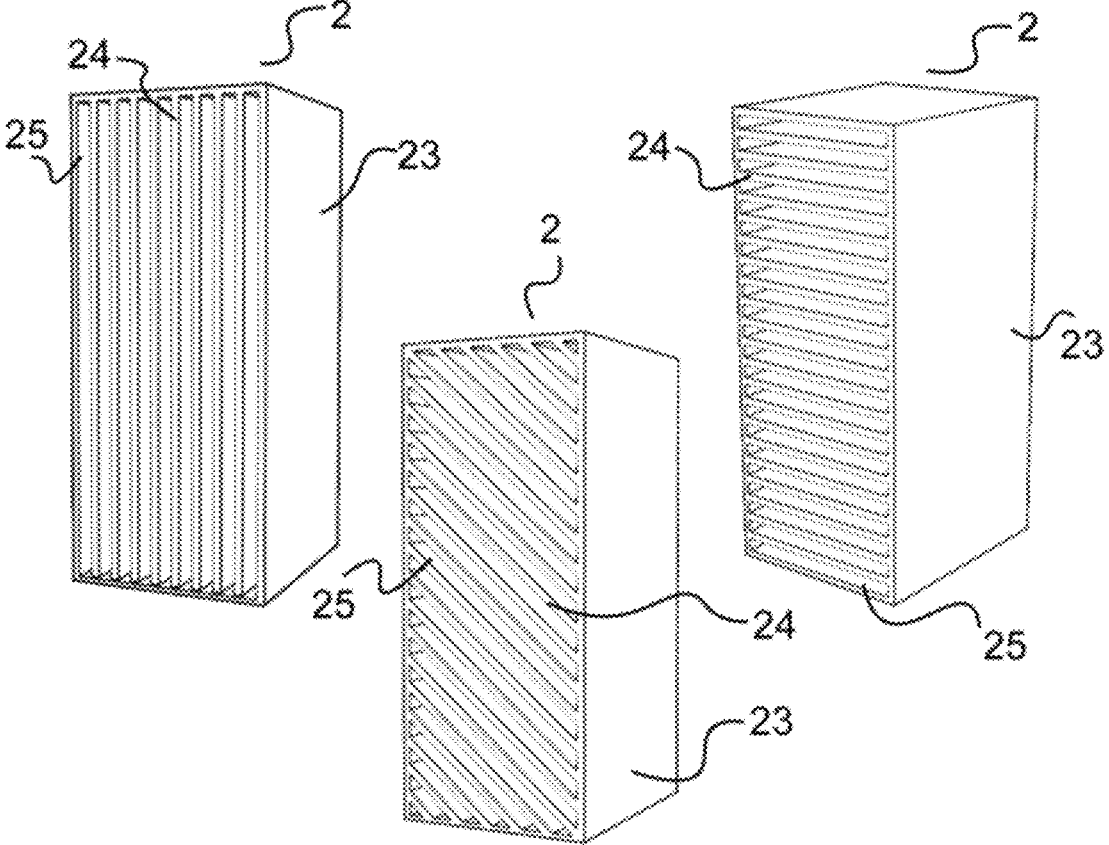
FIG. 9 is a schematic diagram of a ventilation component having baffles of different directions in accordance with one embodiment.
Figure 11:
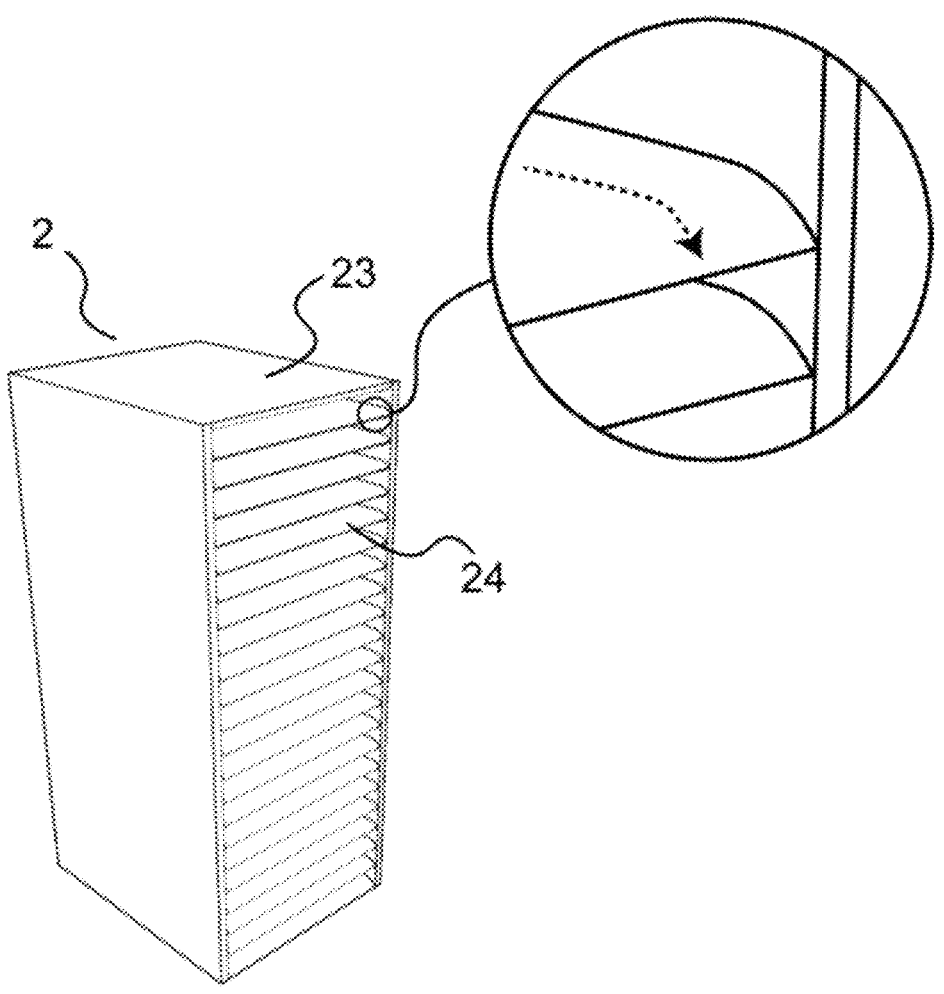
FIG. 11 is a schematic diagram of a ventilation component with a sharp-cornered intake end in accordance with one embodiment.
Figure 12:
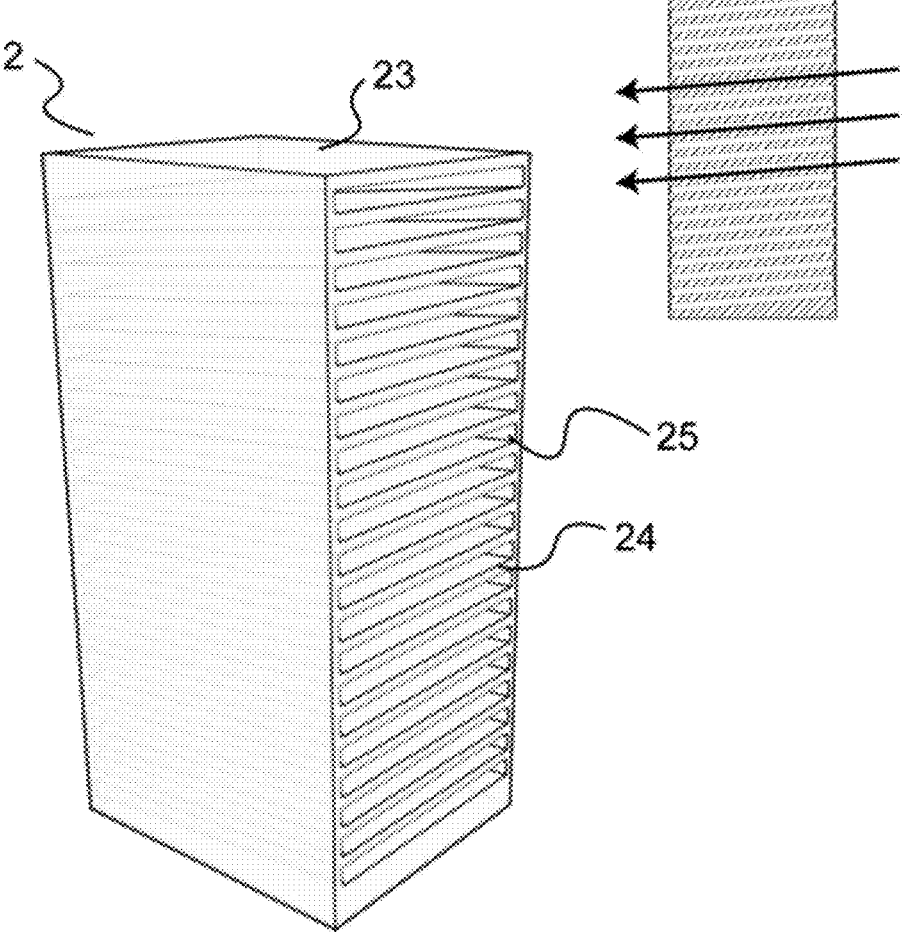
FIG. 12 is a schematic diagram showing the gap planes of a ventilation component not parallel to the horizontal plane in accordance with one embodiment.
Figure 13:
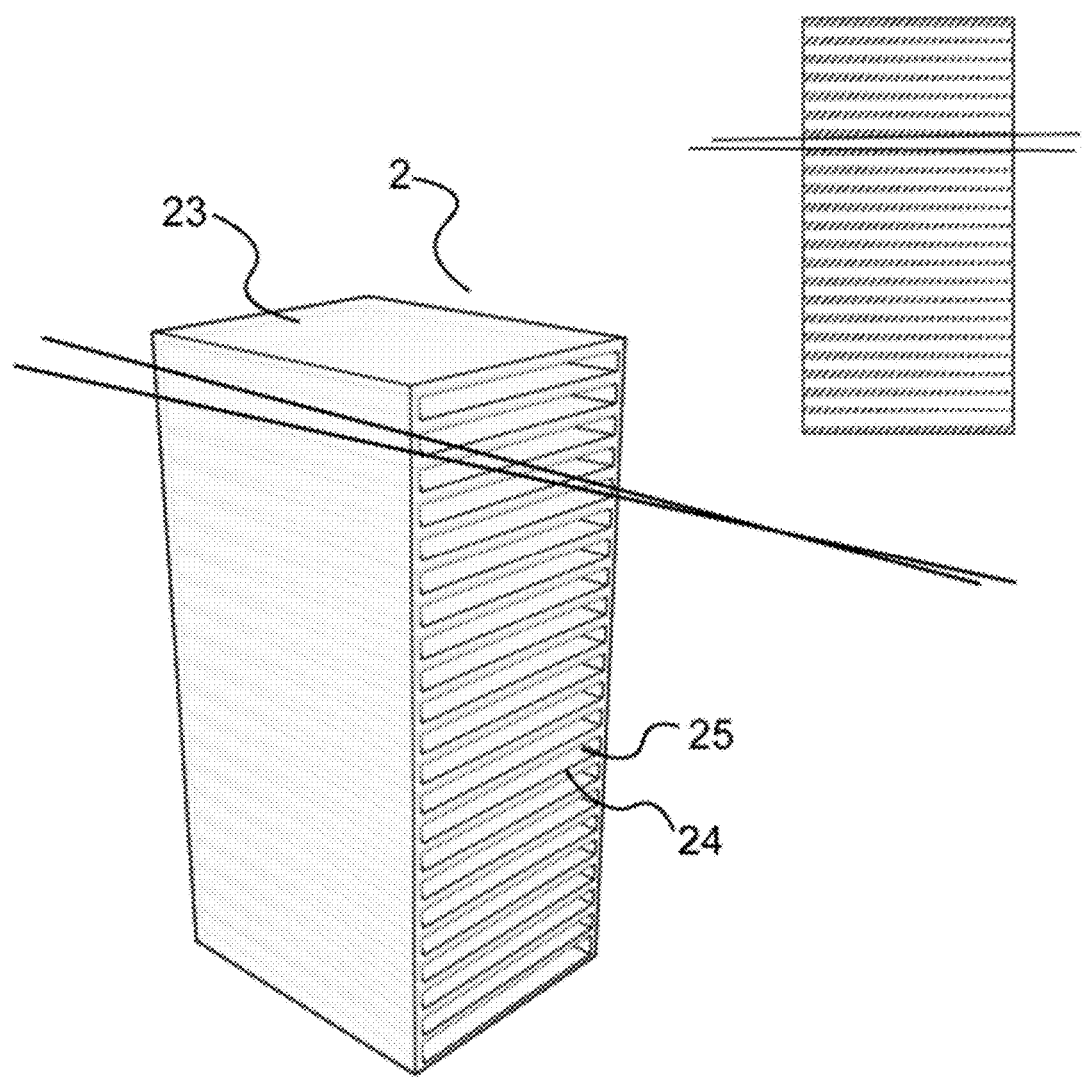
FIG. 13 is a schematic diagram of a ventilation component having gap channels with a tapered space in accordance with one embodiment.
Figure 14:
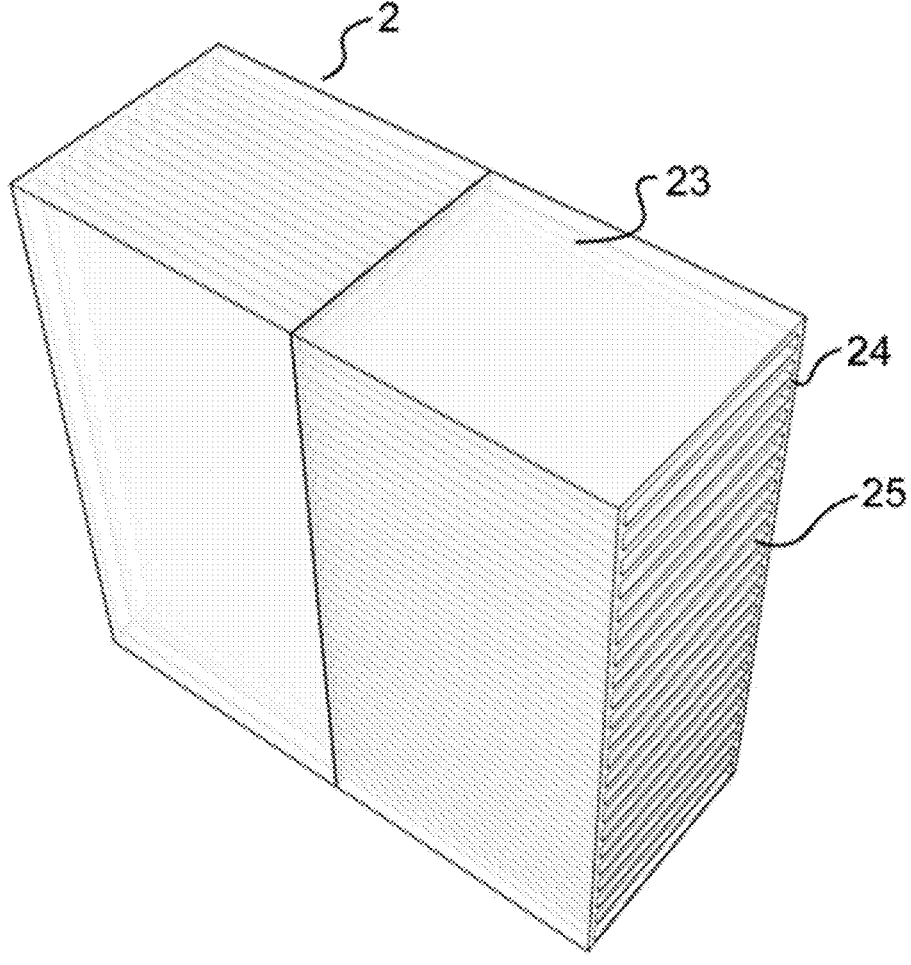
FIG. 14 is a three-dimensional schematic diagram of a ventilation component in accordance with one embodiment.
Figure 15:
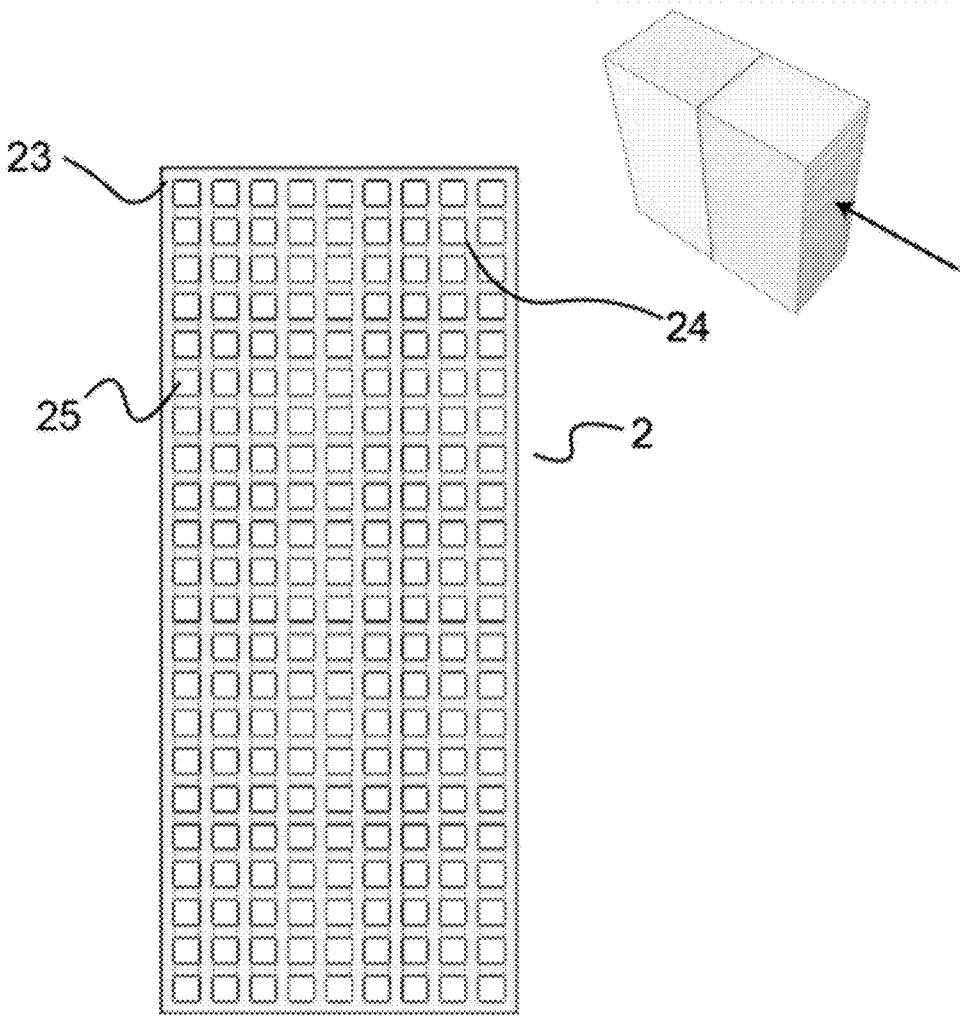
FIG. 15 is an orthographic view of a ventilation component in accordance with one embodiment.
Figure 16:
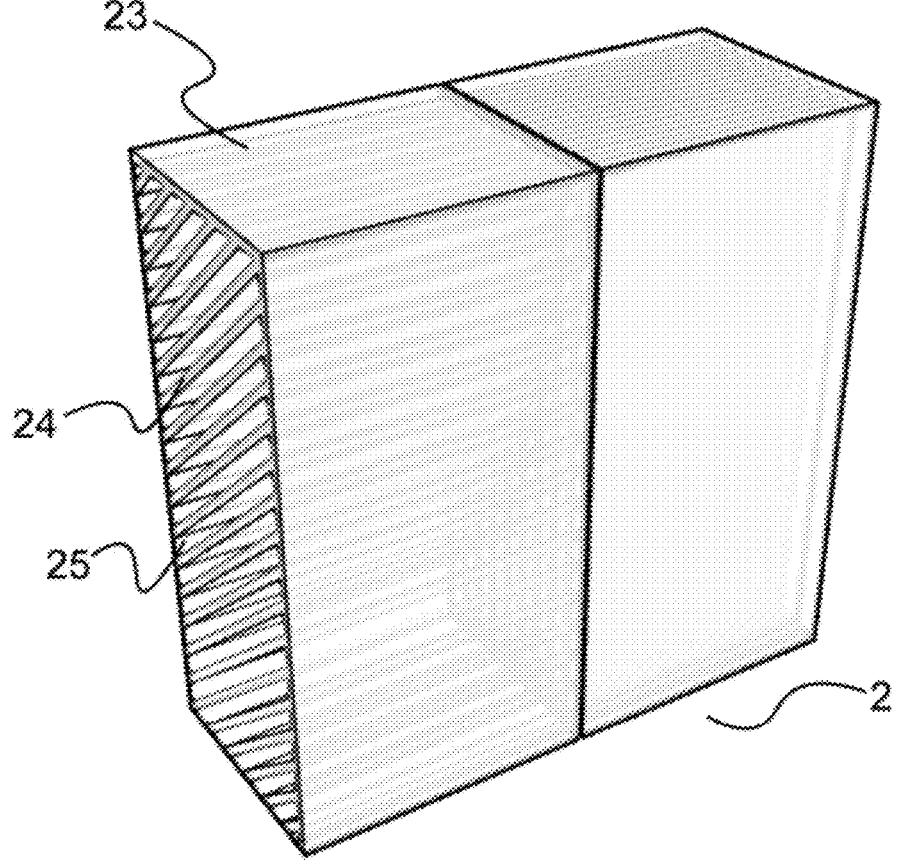
FIG. 16 is a three-dimensional schematic diagram of another form of a ventilation component in accordance with one embodiment.
Figure 17:
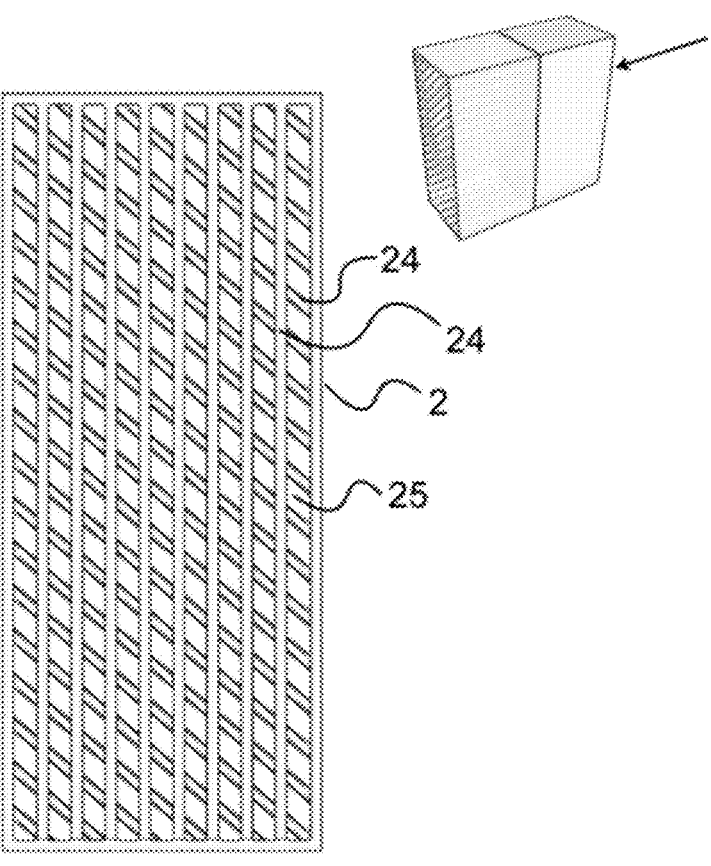
FIG. 17 is an orthographic view of another form of a ventilation component in accordance with one embodiment.
Figure 18:
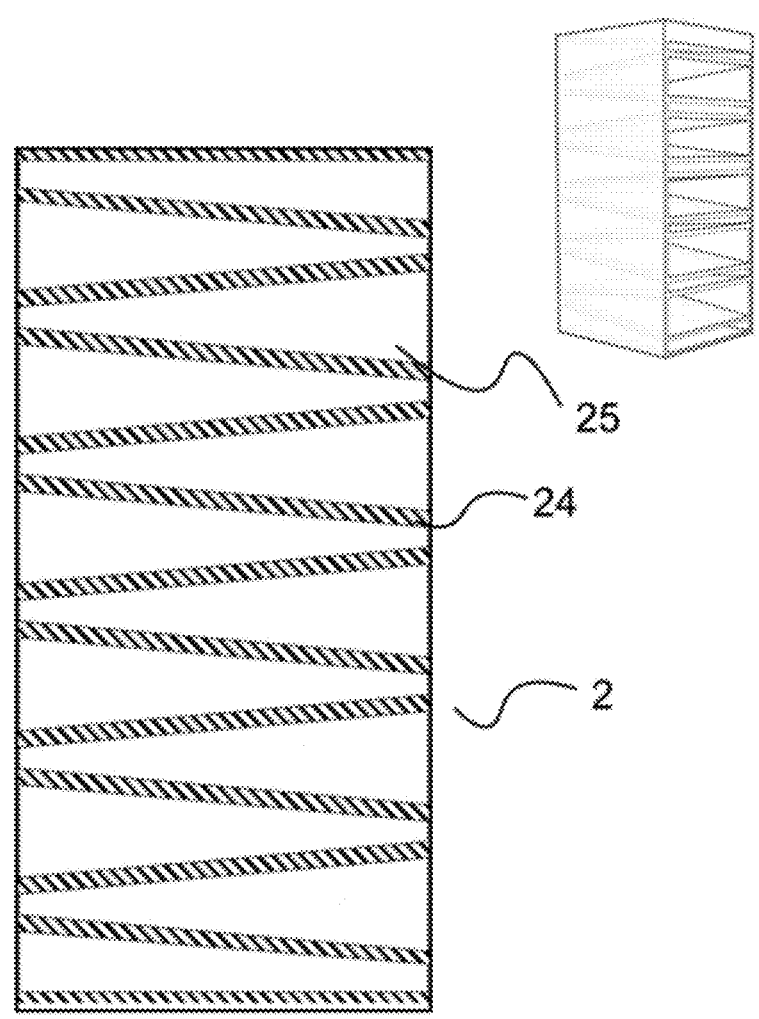
FIG. 18 is a cross-sectional schematic diagram of another form of a ventilation component in accordance with one embodiment.

Specifically, the ventilation component 2 internally includes at least one form of baffles 24 spaced at certain intervals, configured to divide the airflow into multiple smaller flow units. In at least one form, the interval between at least two baffles 24 is equal. In some special cases, the baffles 24 can also have various different distances between them, and intervals between each baffle 24 create gap channels 25 through which the airflow passes. The internal space of the ventilation component 2 is divided into multiple uniform sections by the baffles 24. Typically, the baffles 24 are thin plates with a thickness of 3 mm or less. The function of the baffles 24 is to divide and streamline the air entering the noise-reducing air passage 1 (as shown in FIG. 5, streamlining originally turbulent airflow into a smooth and uniform flow). Since the basic form of the ventilation component 2 is a set of multiple baffles 24 arranged within a specific shape of the peripheral wall 23, intervals between multiple baffles 24 create gap channels 25 through which the airflow passes. Therefore, the arrangement of baffles 24 within the peripheral wall 23 of the ventilation component 2 can have multiple directions; their arrangement within the ventilation component 2 can be parallel to the horizontal plane or the baffles 24 can form an angle with the horizontal plane. Baffles 24 can also be arranged in any other direction. In one scenario, within the orthographic view from the plane of the intake end (as indicated by the arrows in FIG. 15), baffles 24 of at least two different directions are provided and the baffles 24 of different directions intersect each other (as shown in FIGS. 15 and 17, which depict two different intersection methods). This arrangement can take two forms: baffles 24 of different directions aligned along the line connecting the intake end 21 and the exhaust end 22 (as shown in FIGS. 15-17, with one ventilation component in front of another), or baffles 24 of different directions intersecting perpendicular to the line connecting the intake end 21 and the exhaust end 22 (with one ventilation component above another). The specified alignment direction of baffles 24 helps guide the flow path of the airflow and prevents backflow. There are two methods for specifying the angle of rotation of baffles 24: rotating the baffles 24 a certain angle in their alignment direction (as shown in FIGS. 12 and 18), or rotating the baffles 24 around an axis perpendicular to their alignment direction (as shown in FIG. 9). The primary function of baffles 24 is to divide the larger (incoming) airflow into smaller flow units (defined here as less than one-fourth, preferably less than one-eighth, of the original larger airflow). Thus, designing baffles 24 to have sharp corners at the intake end 21 helps better divide the airflow, effectively reducing noise generated by airflow hitting the walls. Furthermore, when both walls forming gap channel 25 at the intake end 21 have chamfers, this expands the gap area at the intake end 21 while forming an expanded opening at the intake end of gap channel 25. This configuration makes it easier for airflow to enter the ventilation component 2 and further increases the airflow's speed and volume, enhancing the efficiency of the ventilation component 2 and reducing airflow turbulence and noise, thereby achieving better noise reduction effects (as shown in FIG. 11). Additionally, baffles 24 can also have a taper; when baffles 24 are tapered, the gaps formed by multiple baffles 24 also have a taper. In one scenario, this taper allows at least one gap channel 25 to have a draft angle with a range between 0.1° to 2°, also serving to enhance the ventilation efficiency of the ventilation component 2 and reduce airflow turbulence and noise (as shown in FIG. 13). It is evident that by altering the form of baffles 24, various forms of the ventilation component 2 can be achieved. Due to its simple structure, the ventilation component 2 can be upgraded and modified to optimize the noise-reducing air passage 1 and the overall noise and comfort of use of the respiratory-related device.

Figure 10:
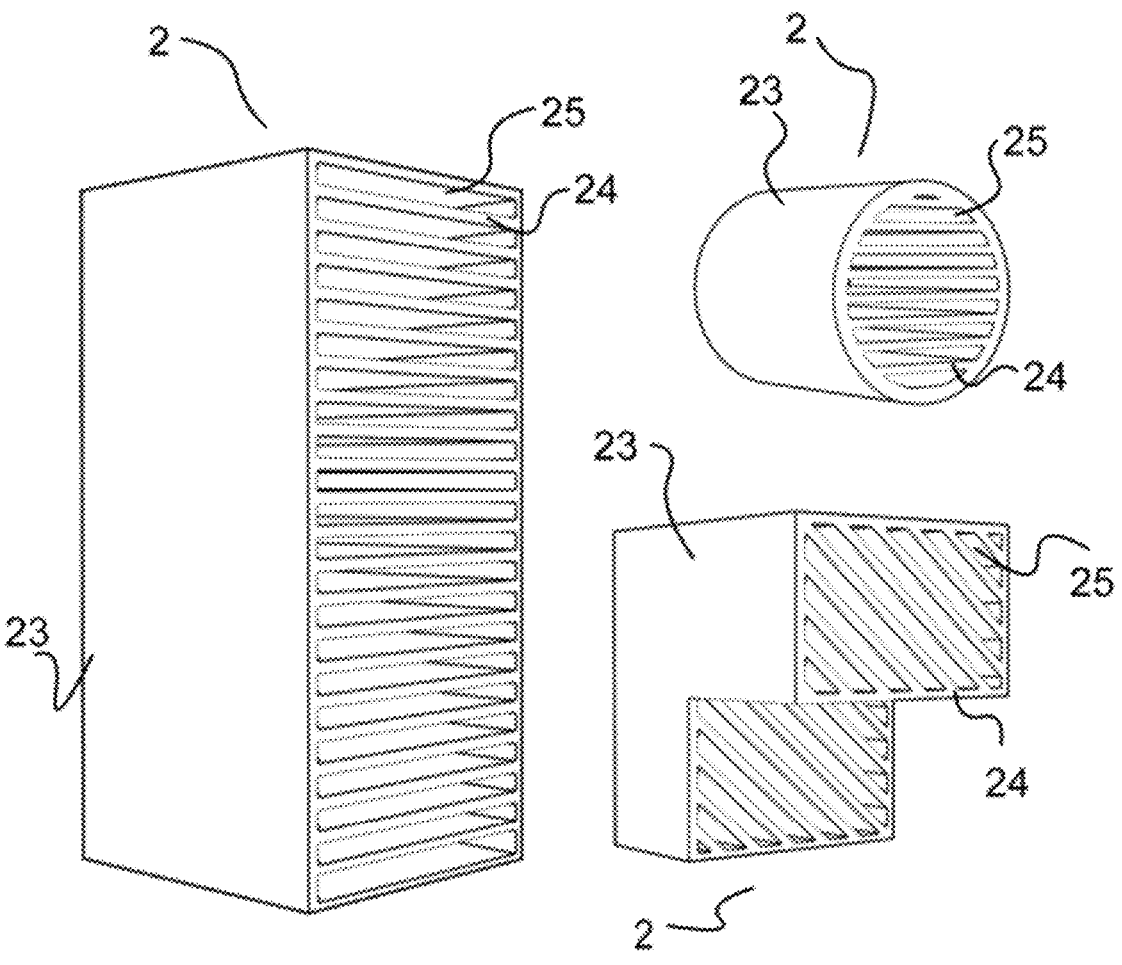
FIG. 10 is a schematic diagram of a ventilation component having different external shapes in accordance with one embodiment.

The ventilation component 2 also includes gap channels 25, formed by the spaces between baffles 24 arranged at certain intervals. Typically, the shape of the gap channel 25 is square, but it can also be circular, diamond-shaped, elliptical, or other shapes. If the path of airflow through the gap channel 25 is too short, the ventilation component 2 cannot effectively disperse the airflow, resulting in poor noise reduction. Therefore, it is specified that straight lines connecting each intake end 21 center to its corresponding exhaust end 22 center of the gap channels are parallel, and a length of the straight lines is at least 10 mm. To ensure smooth passage of gas, the intervals between the baffles are at least 0.8 mm, preferably ranging from 0.8 mm to 2.2 mm. The ventilation component 2 includes a peripheral wall 23, which surrounds the baffles 24 and gap channels 25. To allow sufficient airflow through the ventilation component 2, the total area of the gap channels 25 at the exhaust end 22 is set to be at least 0.2 times the area enclosed by the peripheral wall 23 at the exhaust end 22. Additionally, because the structure of ventilation component 2 is simple, and its primary component is not the peripheral wall 23 but its internal structure, the shape of the peripheral wall 23 can be adjusted according to the different spatial forms inside the noise-reducing air passage 1. For example, if there is a pipe structure similar to an inlet pipe inside the noise-reducing air passage 1, the peripheral wall 23 of the ventilation component 2 can flexibly be transformed into a circular shape to match the pipe structure of the inlet pipe. The ventilation component 2 can also have a square, hexagonal, or other shaped peripheral wall 23. Such designs ensure that the ventilation component 2 perfectly fits with various forms inside the noise-reducing air passage 1, thereby enhancing the applicability and flexibility of the ventilation component 2 (as shown in FIG. 10). In this way, the ventilation component 2 can adapt to the changes of the internal structure within the noise-reducing air passage 1 and provide reliable noise reduction. When its shape is square, testing comparing various length-to-width ratios of the ventilation component 2 has determined that a length-to-width ratio between 0.1 to 1 offers the best noise reduction performance.

Figure 25:
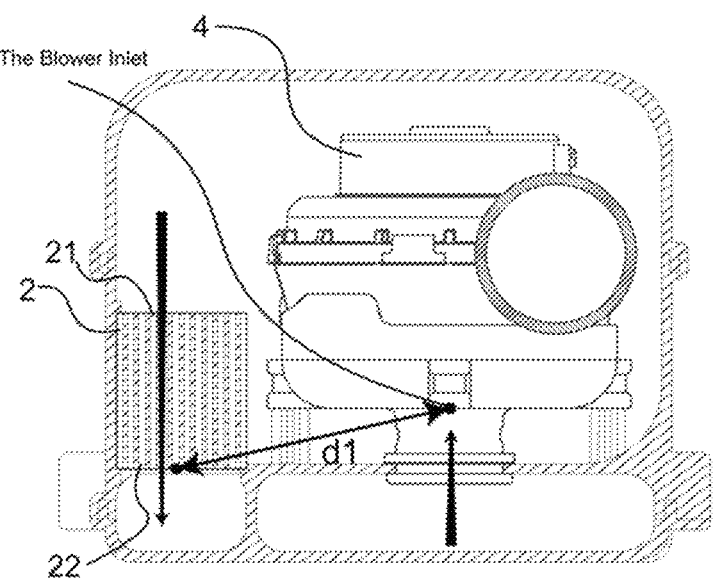
FIG. 25 is a schematic diagram showing the positional relationship between the ventilation component and the blower in accordance with one embodiment.
Figure 26:
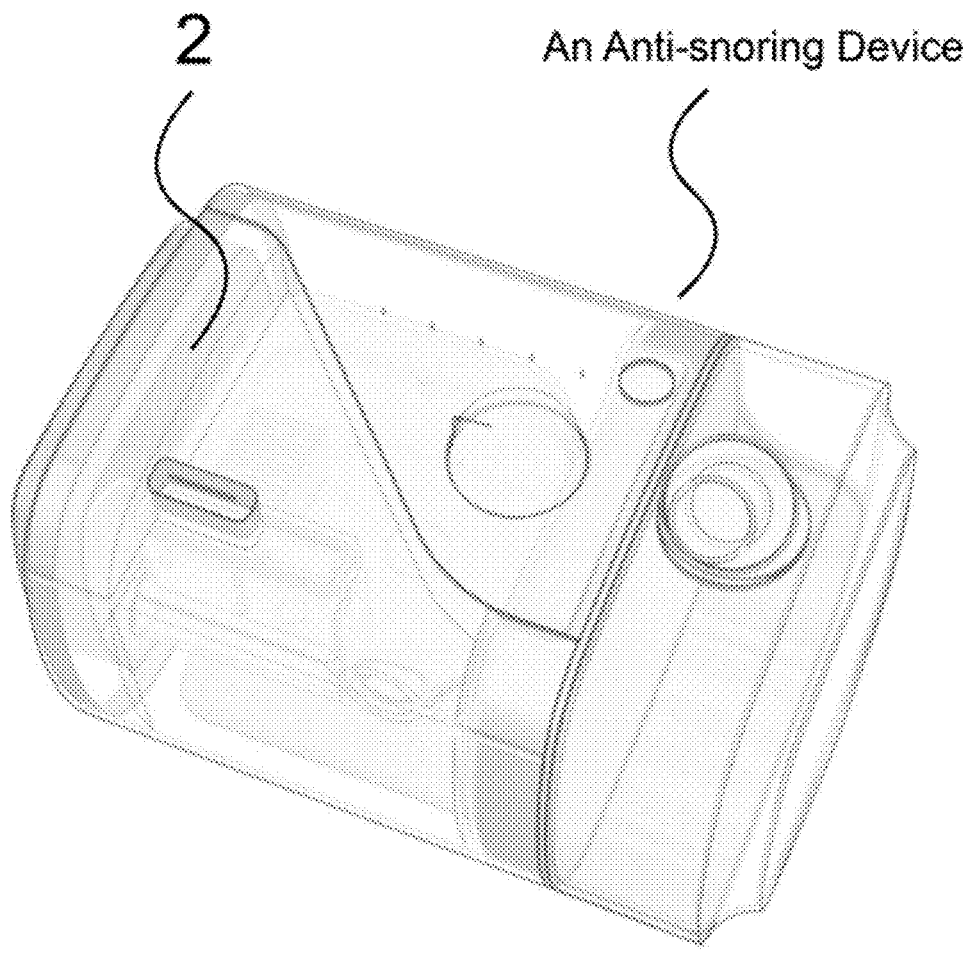
FIG. 26 is a structural schematic diagram of the ventilation component within the anti-snoring device in accordance with one embodiment.

The ventilation component 2 includes an intake end 21 and an exhaust end 22. The intake end 21 is configured to receive airflow into the ventilation component 2, and the exhaust end 22 is configured to allow airflow to exit from the ventilation component 2. The ventilation component 2 is provided within chambers formed by the casing of the noise-reducing air passage 1. The casing has an inner wall 3. To ensure better noise reduction by the ventilation component 2 within the noise-reducing air passage 1, it is crucial to position the ventilation component 2 appropriately. To ensure that there is sufficient gap space for gas to flow into the ventilation component 2, the distance between the exhaust end 22 of the ventilation component 2 and its opposing inner wall 3 of the casing is set to at least 1.5 times the width of the ventilation component 2. Typically, the distance between the exhaust end 22 of the ventilation component 2 and its opposing inner wall 3 of the casing is at least 5 mm. At least two chambers are provided within the casing of the noise-reducing air passage 1. When the noise-reducing air passage 1 is divided into upper and lower chambers, the ventilation component 2 can be placed in several ways. In one case, the ventilation component 2 can be positioned within the noise-reducing air passage 1 such that gas passes through the ventilation component 2 vertically (perpendicular to the horizontal plane). This means that the noise-reducing air passage 1 includes two chambers, the ventilation component 2 communicates with the two chambers, and parts of the ventilation component 2 are present within the two chambers. Alternatively, the ventilation component 2 may only be present in one of the chambers within the casing of the noise-reducing air passage 1, and reduce the noise of the gas in that chamber. In some instances, it is also feasible for the ventilation component 2 to be provided within the noise-reducing air passage 1 in a way that the direction of the gas passing through the ventilation component 2 is horizontal rather than vertical, as the ventilation component 2 is compact enough to be arranged efficiently within the respiratory device without occupying excessive space. Additionally, to avoid noise overlap between the exhaust end 22 of the ventilation component 2 and the blower inlet, the straight-line distance d1 between the exhaust end 22 of the ventilation component 2 and the blower inlet is set to be less than or equal to 15 mm (as shown in FIG. 25). When the direction of the gas flowing through the ventilation component 2 is parallel to the direction of the gas entering the blower 4 (as shown in FIG. 25), the noise-reducing air passage 1 achieves further noise reduction.

In another embodiment, the intake end 21 and exhaust end 22 of the ventilation component 2 are formed by two or more planes, such as a step-shaped exterior of the ventilation component 2.

In yet another embodiment, the opening at the intake end 21 of the ventilation component 2 is larger than the opening at the exhaust end 22.

Embodiment 2

Figure 19:
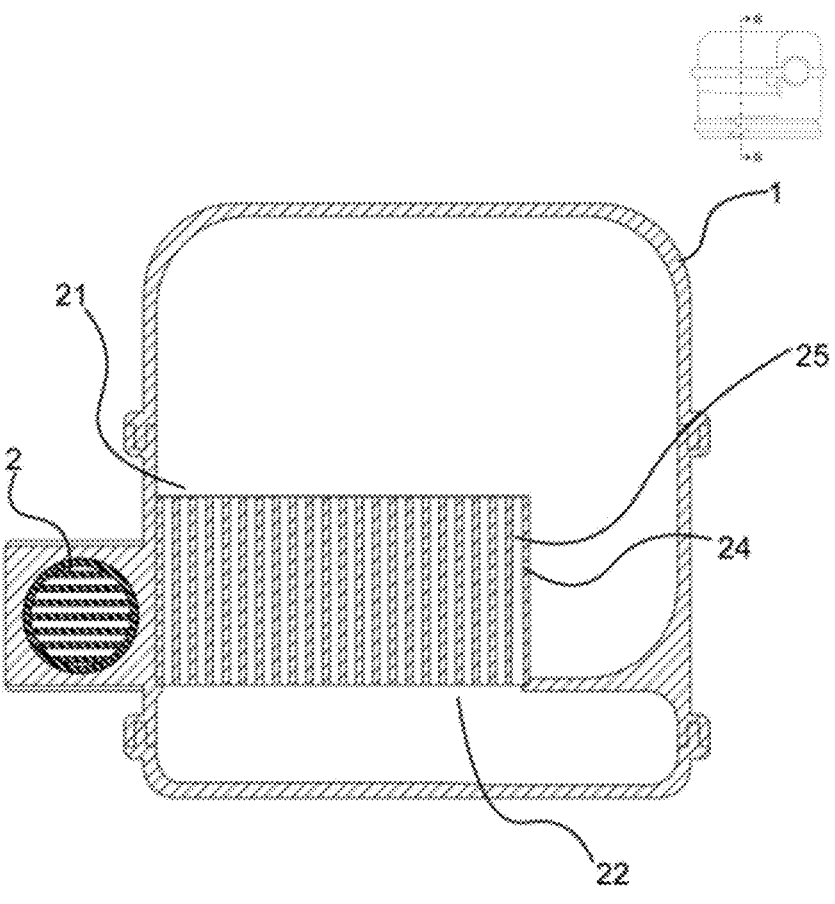
FIG. 19 is a cross-sectional diagram of two different forms of ventilation components for use within the noise-reducing air passage in accordance with one embodiment.
Figure 20:
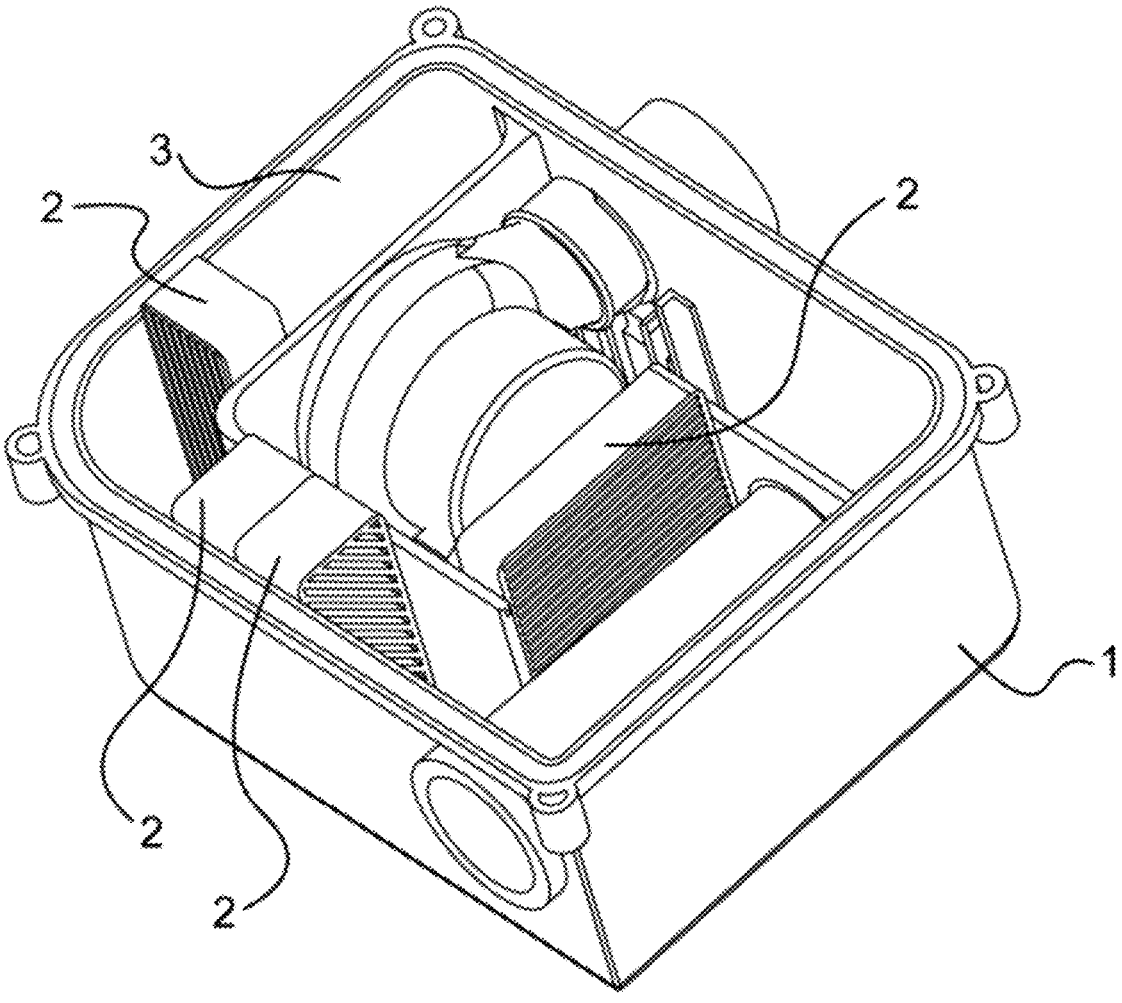
FIG. 20 is a schematic diagram of different forms of a ventilation component for use within the noise-reducing air passage in accordance with one embodiment.

This embodiment provides a ventilation component 2 for use within a noise-reducing air passage 1 of respiratory-related devices like PAP machines, as shown in FIGS. 19 and 20. This embodiment offers a cross-sectional diagram and usage diagram of the ventilation component 2. As shown in FIGS. 19 and 20, the difference between this embodiment and Embodiment 1 lies in the noise-reducing air passage 1 having two or more ventilation components 2 cooperating for noise reduction. The design flexibility of the ventilation component 2 allows it to adapt to various spatial layouts. For example, the ventilation component 2 can adopt various external forms to fit different spatial configurations. Thus, when the noise-reducing air passage 1 includes two or more spatial forms, such as an air passage with an inlet pipe, a circular-shaped ventilation component 2 within the inlet pipe can be used alongside a square-shaped ventilation component 2 within the chamber of the noise-reducing air passage 1. Moreover, the same type of noise-reducing air passage 1 can also have ventilation components 2 with baffles 24 at the same or different angles to achieve more efficient noise reduction. The coordination between the ventilation components 2 is also varied; they can be spaced apart within the noise-reducing air passage 1 in non-adjacent positions, allowing the airflow to be divided into smaller flow units, then recombined and divided again. Placing ventilation components 2 at different positions helps streamline and mitigate turbulent airflow within parts of the noise-reducing air passage 1, achieving noise reduction over a larger area. The arrangement can also be such that two or more adjacent ventilation components 2 extend the gap channels 25 for noise reduction. For instance, when two ventilation components 2 with the same structure are used adjacently (where the intake end 21 of one ventilation component 2 tightly fits against the exhaust end 22 of another ventilation component 2), they form a continuous airflow path between them, effectively lengthening the length of the ventilation component 2, resulting in a more elongated gas flow path within the channel, which prolongs the stay of the air within the channel, further enhancing noise reduction. When two different structural forms of the ventilation component 2 (with different angles of baffles 24) are used adjacently, the airflow is first divided into smaller flow units upon entering the first form of ventilation component 2, and as the second form of ventilation component 2 has baffles 24 at different angles, the airflow is again divided by the baffles 24 after exiting the first form and entering the second form. This process causes the already divided airflow to be further subdivided into even smaller flow units. Through this continuous division, the airflow gradually slows down, and the noise in the airflow is more effectively dispersed and reduced. The cooperative use of different forms of ventilation components 2 can effectively optimize the dynamic characteristics of the airflow, making the airflow within the channel smoother and quieter. This design allows for flexible combination of ventilation components 2 according to specific needs to achieve optimal noise reduction effects.

In another embodiment, baffles 24 of different directions are present within a ventilation component 2, where these baffles 24 have a front-to-back relationship inside the ventilation component 2. Near the intake end, there are multiple baffles 24 arranged parallel to the horizontal plane, followed immediately by multiple baffles 24 arranged perpendicular to the horizontal plane extending towards the exhaust end 22. The baffles 24 of different directions are connected at their adjacent ends, having the same peripheral wall 23. Alternatively, the directions of the baffles 24 can be arbitrary, and their proportional length within the ventilation component 2 can also be arbitrary.

Embodiment 3

Figure 21:
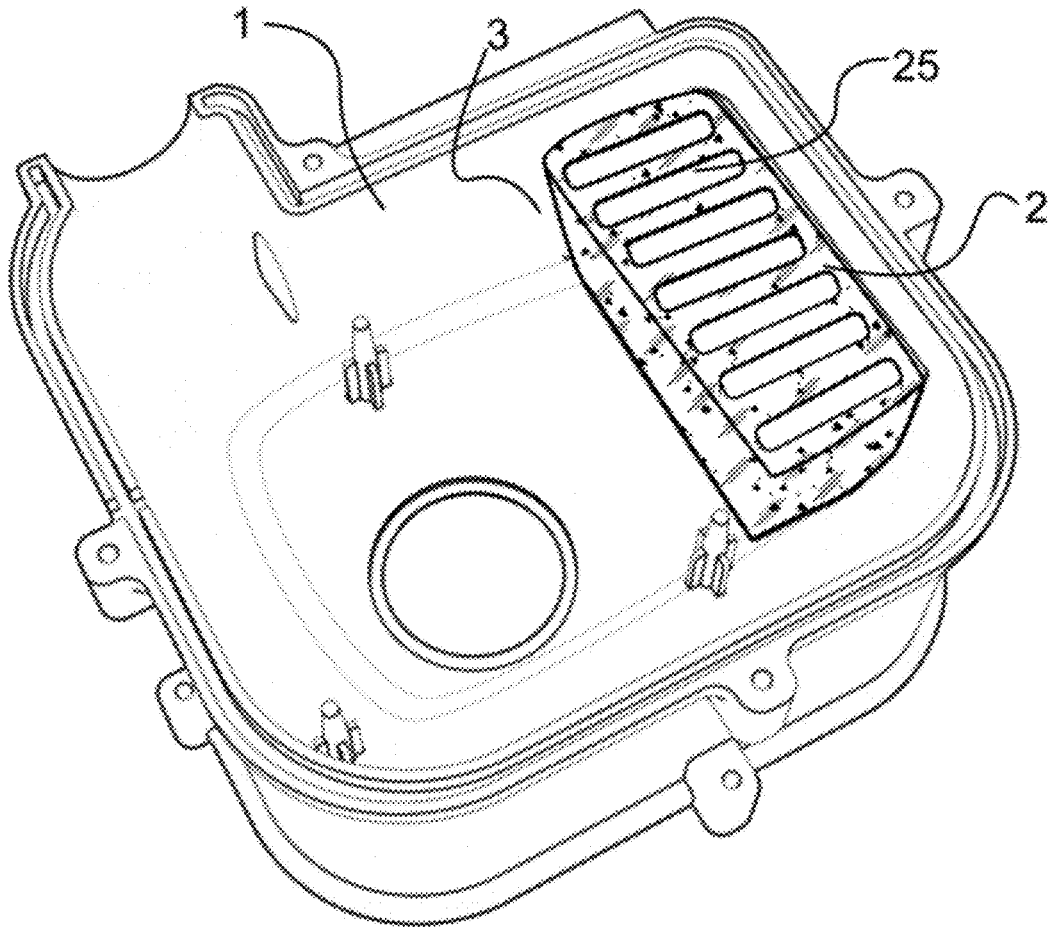
FIG. 21 is a schematic diagram of a ventilation component made of another material for use within the noise-reducing air passage in accordance with one embodiment.

In another embodiment, a ventilation component 2 configured for use within the noise-reducing air passage 1 of respiratory-related devices such as PAP machines is provided. Refer to FIG. 21 for a schematic diagram of the use of the ventilation component 2. This embodiment differs from Embodiment 1 in that the ventilation component 2 is made from a different material than that used in Embodiment 1. The use of different materials for the ventilation component 2 can also achieve noise reduction, for example, by using silicone to form holes, a method that follows the core structural principle of the ventilation component 2 provided by Embodiment 1, which involves dividing and streamlining turbulent airflow through internal holes. The elasticity and softness of the silicone-based ventilation component 2 enable it to absorb vibrations and noise from the noise-reducing air passage 1, thereby lowering the overall noise levels and enhancing the sleep quality and therapeutic outcomes for patients. Additionally, the durability and stability of silicone are prominent features. Compared to other materials, the silicone-based ventilation component 2 withstands prolonged use with little aging or deforming. This means patients can rely on this type of ventilation component 2 over the long term without concerns about performance degradation or the need for replacement, thereby reducing the maintenance costs of respiratory-related devices. The silicone-based ventilation component 2 not only effectively reduces noise but also maintains smooth airflow, providing a quieter and more comfortable treatment experience for patients. Furthermore, the silicone-based ventilation component 2 exhibits excellent stability. It maintains stable performance under various environmental conditions, unaffected by temperature changes or humidity. This means that even in humid or high-temperature environments, the ventilation component 2 continues to perform its noise reduction and ventilation functions reliably, offering dependable therapeutic support to patients and ensuring that this form of ventilation component 2 maintains its excellent performance despite environmental changes.

Embodiment 4

Figure 22:
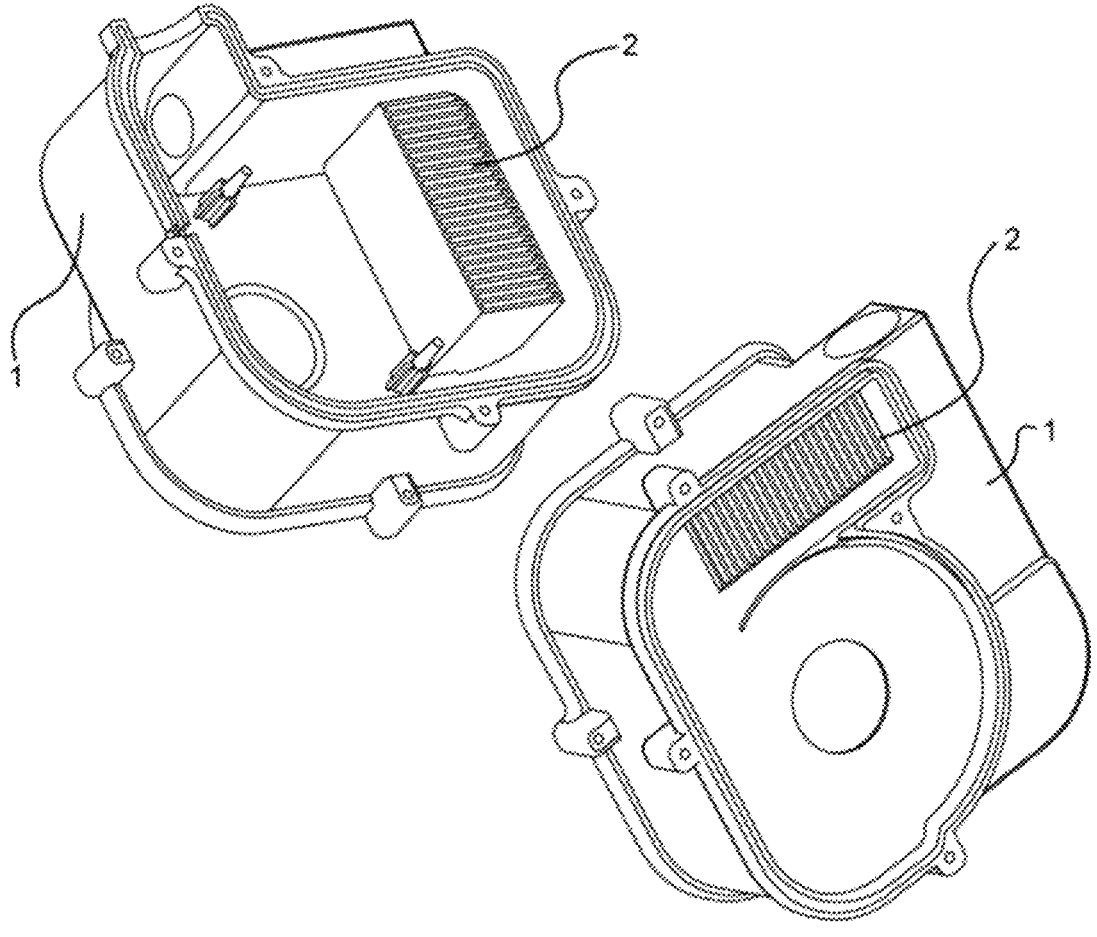
FIG. 22 is a schematic diagram of the ventilation component being integrally formed with the casing of the noise-reducing air passage in accordance with one embodiment.
Figure 23:
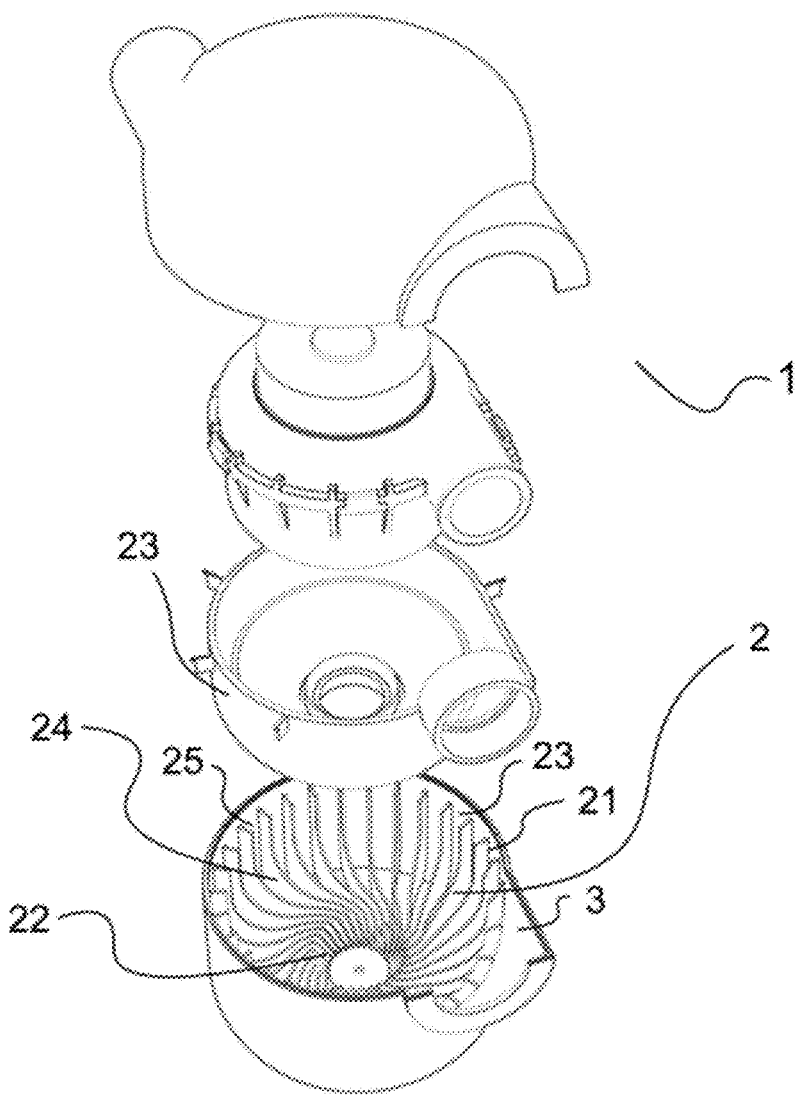
FIG. 23 is an exploded schematic diagram of another form of ae ventilation component being integrally formed with the casing in accordance with one embodiment.
Figure 24:
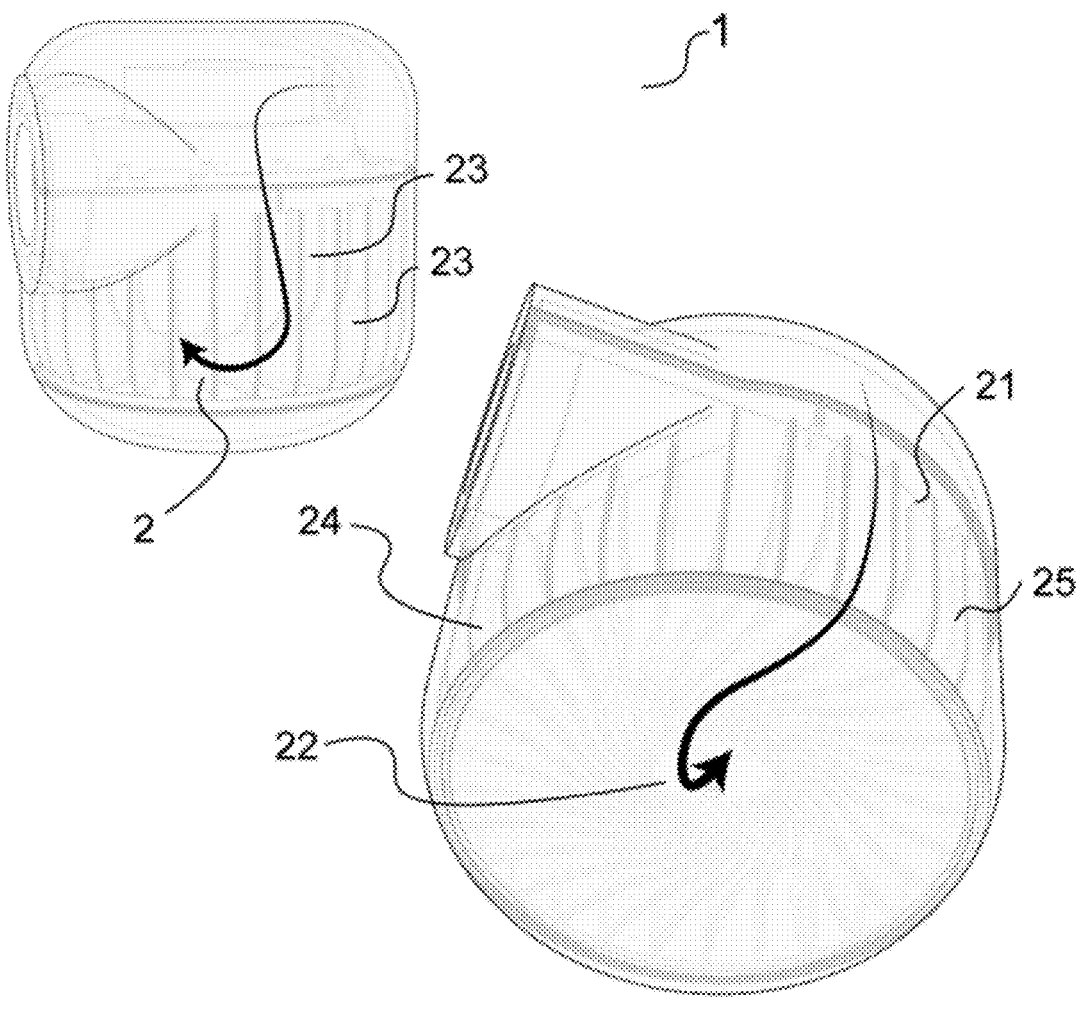
FIG. 24 is a schematic diagram of another form of the ventilation component being integrally formed with the casing in accordance with one embodiment.

This embodiment provides a ventilation component 2 for use within the noise-reducing air passage 1 of respiratory-related devices such as PAP machines. Refer to FIGS. 22-24 for three-dimensional schematic diagrams of the ventilation component 2. This embodiment as shown in FIGS. 22-24 differs from Embodiment 1 in that the ventilation component 2 is integrally formed with the casing of the noise-reducing air passage 1 (as shown in FIG. 22). In this configuration, the structure of the ventilation component involves baffles that merge with the wall of the casing of the noise-reducing air passage 1, with the peripheral wall of the ventilation component 2 being part of the casing of the noise-reducing air passage 1 itself. The design of ventilation component 2 is versatile; its peripheral wall 23 can take multiple forms, even being composed of the walls of chambers (as shown in FIGS. 23 and 24). The functional structure of the ventilation component 2 is formed by channels formed by baffles 24. When baffles 24 are shaped to have a specific form, this configuration can guide or extend the gas flow path. For example, in this embodiment, as illustrated in FIGS. 21 and 22, the baffles 24 are arranged irregularly or in a patterned curvature along the inner walls 3 of the chamber of the noise-reducing air passage 1. This design, compared to a linear arrangement of baffles 24, more effectively guides the airflow and extends the gas flow path within the noise-reducing air passage 1. This design not only aids in optimizing the flow of air but also adapts to more complex structures of the inner walls 3 of the chamber.

The implementation of the ventilation component provided by this disclosure at least includes the following beneficial effects:

1. The ventilation component features a simple and reliable structure that enhances the stability of the noise-reducing air passage, while also being easy to install and reducing costs. Unlike existing market solutions that use foam provided within the noise-reducing air passage for primary noise reduction or complex noise-reducing components made from multiple materials, this disclosure utilizes a ventilation component made from a single material. This simple structure offers clear advantages in terms of structure, cost, production efficiency, and stability. Firstly, the ventilation component of this disclosure can reduce noise by at least 2 decibels, not only providing excellent noise reduction but also achieving regulatory noise level. Its structure, consisting only of a peripheral wall and the baffles surrounded by the peripheral wall, simplifies the form and avoids complex, intricate connections, thus reducing the risk of potential faults and damage due to structural complexity, providing a solid foundation for the long-term stable operation of respiratory machines. Moreover, because of its simple structure, the ventilation component is easier to maintain and repair, reducing the maintenance costs and time for the respiratory-related devices. Secondly, the ventilation component is relatively small in size, making it more convenient to install inside the noise-reducing air passage without occupying excessive space. Multiple ventilation components can also be combined within the air passage, resulting in a more compact overall structure of the respiratory machine. Additionally, the simplicity and ease of installation of the ventilation component allow assembly personnel to easily assemble it, saving time and labor costs during the production phase and further enhancing production efficiency. Furthermore, as the ventilation component is formed from a single material and has a basic structure, it itself is a basic unit component, the manufacturing process is simplified and costs are more controllable. Specifically, due to its simple structure and uniform material, manufacturers can more easily engage in mass production, and due to its separability, producers and developers can further reduce costs through material optimization and process improvements. Consequently, the ventilation component of this disclosure also offers the advantage of lower costs, providing patients with a high cost-effective product while also facilitating technological innovation and cost reduction in the respiratory machine industry.

2. By using accurate scientific data and correct theoretical foundations, the structure of the ventilation component is configured to achieve more efficient noise reduction. (1) After determining the optimal form of the ventilation component, its structure and position data are standardized, and multiple simulations and experiments are conducted to ensure the component achieves optimal performance in this form. First, the area of the gap channels within the ventilation component is specified, as these channels are the sole pathways for air to pass through the chamber within the chamber at its position. Therefore, the size of the gap channels determines whether there is sufficient air flow entering the blower for pressurization, and overly narrow gap channels can produce noise when air flows through them at certain speeds. Thus, the interval between the baffles is set to be greater than 0.8 mm. Conversely, if the gap channels are too large, the baffles cannot function well to reduce noise. Thus, the interval between the baffles is set to be less than 2.2 mm. (2) Additionally, the noise level is also related to the length of the ventilation component (the length of the gap channels). When the gas flows through the ventilation component, although the airflow is divided into smaller flow units by the baffles, gap channels with a too-short length can cause the airflow to immediately recombine after division, making the baffles unable to achieve the intended effect of reducing turbulence and noise, thereby impacting noise reduction. Hence, the length of each gap channel in the ventilation component is set to be at least 10 mm. These data are derived from comparing information and conducting multiple repetitive experiments by placing different forms of ventilation components in the same noise-reducing air passage and then testing different forms of ventilation components used in the first experiment in another noise-reducing air passage. This process yields conclusions that withstand repeated testing, leading to the design of the optimal structure for the ventilation component in this disclosure.

3. The ventilation component exhibits strong adaptability, allowing for flexible application according to different internal structures of noise-reducing air passages, while impacting airflow less and maintaining its fluidity. The core element of the ventilation component lies in its structure configured to divide and streamline airflow for noise reduction, enabling the external shape of the ventilation component to vary as needed. (1) In typical scenarios, to facilitate placement in chambers within the noise-reducing air passage, the ventilation component adopts a rectangular casing. In some cases, when it needs to be positioned within tubes of the air passage such as the inlet pipe, its appearance can be altered to have a circular peripheral wall to fit the pipe. It is evident that the ventilation component can also take on any shape other than rectangular or circular, such as elliptical or conical, based on the internal structure of the noise-reducing air passage. (2) The ventilation components can be freely combined, such that in the orthographic view from the plane of the intake end, the baffles of at least two directions are provided and the lines on which baffles of different directions lie intersect each other, forming a more effective ventilation component combination. There are two possible arrangements for this free combination: either the baffles of different directions are aligned in the line connecting the intake end and exhaust end (with one ventilation component in front of the other), or the baffles of different directions are aligned perpendicular to the line connecting the intake end and exhaust end (with one ventilation component above the other), making the ventilation component more effective and flexible. (3) Additionally, pairing the ventilation component with noise-reducing materials such as foam or silicone can further lower the overall noise of the anti-snoring device. The ventilation component divides larger airflows into smoother streams to reduce noise, while the noise-reducing materials absorb sound energy and convert it into kinetic energy, dissipating noise and achieving further noise reduction. This flexibility allows the ventilation component to adjust according to the internal structure and spatial constraints of the air passage, resulting in better matching and noise reduction effects. Thus, the ventilation component is versatile in form, capable of adapting to various shapes and structures of noise-reducing air passages, providing greater applicability and flexibility for noise reduction treatments. Moreover, delivering breathable gas at a specific pressure and flow rate is a crucial outcome for respiratory devices; therefore, ensuring that the placement of the ventilation component within the noise-reducing air passage does not affect the airflow's pressure and flow is vital for the normal operation of respiratory devices. This disclosure achieves this by calculating the appropriate gap width inside the ventilation component, ensuring that while it reduces noise, it does not hinder the ventilation fluidity, thus ensuring the stability and effectiveness of the respiratory device treatment.

The above description of the embodiments of the disclosure is provided with reference to the accompanying drawings. However, the disclosure is not limited to the specific embodiments described above. These specific embodiments are merely illustrative and not restrictive. Those skilled in the art, in light of the teachings of the disclosure, may make many modifications and variations without departing from the spirit and scope of the disclosure as defined by the claims. All such modifications and variations are within the protection scope of the disclosure.

It must be noted that as used herein and in the appended claims, the singular forms "a", "an", and "the" include their plural equivalents, unless the context clearly dictates otherwise.

The invention claimed is:

1. A ventilation component for use in an anti-snoring device, wherein the ventilation component is provided within a noise-reducing air passage of a machine for treatment of respiratory-related disorders, and is configured to divide and streamline gas that flows into the noise-reducing air passage, the ventilation component comprising:
    a peripheral wall;
    an intake end, configured to receive airflow into the ventilation component;
    an exhaust end, configured to allow the airflow to exit from the ventilation component; and
    baffles spaced at intervals, configured to divide the airflow into multiple smaller flow units, wherein the intervals between at least two of the baffles are equal, and the intervals between the baffles create gap channels through which the airflow passes in a first direction;
    wherein a length-to-width ratio of the ventilation component is between 0.1 to 1,
    wherein the baffles are parallel to each other to form the gap channels, and
    wherein all the baffles are planar, parallel and not perpendicular to each other and have a first end directly connected to a first side of the peripheral wall and a second end directly connected to a second side of the peripheral wall.

2. The ventilation component according to claim 1, wherein the baffles form an angle with a horizontal plane.

3. The ventilation component according to claim 1, wherein a casing of the noise-reducing air passage includes an inner wall, and a distance between the exhaust end of the ventilation component and the opposing inner wall of the casing is at least 1.5 times a width of the ventilation component.

4. The ventilation component according to claim 1, wherein two chambers are provided within the noise-reducing air passage, and the ventilation component communicates with the two chambers, and parts of the ventilation component are present within the two chambers.

5. The ventilation component according to claim 1, wherein the ventilation component includes a rigid material.

6. The ventilation component according to claim 5, wherein the rigid material includes one or more of the following materials: polypropylene, polycarbonate, polyethylene terephthalate-1,4-cyclohexane dimethanol ester, polyamide, or polyetheretherketone.

7. A ventilation component for use in an anti-snoring device, wherein the ventilation component is provided within a noise-reducing air passage of a machine for treatment of respiratory-related disorders, and is configured to divide and streamline gas that flows into the noise-reducing air passage, the ventilation component comprising:

at least one intake end, configured to receive airflow into the ventilation component;

at least one exhaust end, configured to allow the airflow to exit from the ventilation component, wherein a distance between the at least one exhaust end of the ventilation component and an opposing inner wall of a casing of the noise-reducing air passage is at least 5 mm;

baffles spaced at intervals, configured to divide the airflow into multiple smaller flow units, wherein the intervals between the baffles create gap channels through which the airflow passes;

a rectangular peripheral wall that surrounds the baffles, wherein a total area of the gap channels at the at least one exhaust end is at least 0.2 times an area enclosed by the peripheral wall of the ventilation component at the at least one exhaust end;

wherein the baffles extend to the peripheral wall of the ventilation component to form the gap channels which extend to the peripheral wall of the ventilation component, and wherein all the baffles are planar, parallel and not perpendicular to each other and are arranged in a second direction.

8. The ventilation component according to claim 7, wherein the ventilation component is provided within the noise-reducing air passage such that the gas passes through the ventilation component in a vertical direction.

9. The ventilation component according to claim 7, wherein a blower is provided within the noise-reducing air passage, and a direction of the gas that flows through the ventilation component is parallel to a direction of the gas that enters the blower.

10. The ventilation component according to claim 9, wherein the blower includes an inlet, and a straight-line distance between the at least one exhaust end of the ventilation component and the inlet is less than or equal to 15 mm.

11. The ventilation component according to claim 7, wherein at least two chambers are provided within the noise-reducing air passage, and the ventilation component is present only within one of the at least two chambers.

12. The ventilation component according to claim 7, wherein the ventilation component and the casing of the noise-reducing air passage are integrally formed.

13. A ventilation component for use in an anti-snoring device, wherein the ventilation component is provided within a noise-reducing air passage of a machine for treatment of respiratory-related disorders, and is configured to divide and streamline gas that flows into the noise-reducing air passage, the ventilation component comprising:

an intake end, configured to receive airflow into the ventilation component;

an exhaust end, configured to allow the airflow to exit from the ventilation component, wherein a distance between the exhaust end of the ventilation component and an opposing inner wall of a casing of the noise-reducing air passage is at least 5 mm;

baffles spaced at intervals, configured to divide the airflow into multiple smaller flow units, wherein the intervals between the baffles create gap channels through which the airflow passes;

a rectangular peripheral wall that surrounds the baffles, wherein a total area of the gap channels at the exhaust end is at least 0.2 times an area enclosed by the peripheral wall of the ventilation component at the exhaust end;

wherein a distance from the intake end to the exhaust end of the ventilation component is at least 10 mm, and wherein all the baffles are planar, parallel and not perpendicular to each other and extend across an entire width of the ventilation component.

14. The ventilation component according to claim 13, wherein the distance between the exhaust end of the ventilation component and the opposing inner wall of the casing of the noise-reducing air passage is at least 1.5 times a width of the ventilation component.

15. The ventilation component according to claim 13, wherein the ventilation component includes a rigid material.

16. The ventilation component according to claim 13, wherein the ventilation component is provided within the noise-reducing air passage such that the gas passes through the ventilation component in a horizontal direction.

17. The ventilation component according to claim 13, wherein a length-to-width ratio of the ventilation component is between 0.1 to 1.

18. The ventilation component according to claim 13, wherein the baffles of the ventilation component are tapered.

19. A ventilation component for use in an anti-snoring device, wherein the ventilation component is provided within a noise-reducing air passage of a machine for treatment of respiratory-related disorders, and is configured to divide and streamline gas that flows into the noise-reducing air passage, the ventilation component comprising:

an intake end, configured to receive airflow into the ventilation component;

an exhaust end, configured to allow the airflow to exit from the ventilation component; and baffles spaced at intervals, configured to divide the airflow into multiple smaller flow units, wherein the intervals between the baffles create gap channels through which the airflow passes;

wherein at least one gap channel has a draft angle with a range between 0.1° to 2°;

wherein the intervals between the baffles are at least 0.8 mm, wherein the baffles are parallel to each other to form the gap channels, and wherein all the baffles are planar, parallel and not perpendicular to each other and extend across an entire width of the ventilation component.

20. The ventilation component according to claim 19, wherein a blower is provided within the noise-reducing air passage and the blower includes an inlet, and a straight-line distance between the exhaust end of the ventilation component and the inlet is less than or equal to 15 mm.

21. The ventilation component according to claim 19, wherein two chambers are provided within the noise-reducing air passage, and the ventilation component communicates with the two chambers, and parts of the ventilation component are present within the two chambers.

22. The ventilation component according to claim 20, wherein a direction of the gas that flows through the ventilation component is parallel to a direction of the gas that enters the blower.

23. The ventilation component according to claim 19, wherein the ventilation component is provided within the noise-reducing air passage, and a distance between the exhaust end of the ventilation component and the opposing inner wall of a casing of the noise-reducing air passage is at least 1.5 times a width of the ventilation component.

24. The ventilation component according to claim 19, wherein the baffles of the ventilation component are arranged in at least two directions.

25. The ventilation component according to claim 19, wherein an opening at the intake end of the ventilation component is larger than an opening at the exhaust end.

* * * * *